US009012180B2

(12) United States Patent
Drapeau et al.

(10) Patent No.: US 9,012,180 B2
(45) Date of Patent: Apr. 21, 2015

(54) USE OF COPPER AND GLUTAMATE IN CELL CULTURE FOR PRODUCTION OF POLYPEPTIDES

(75) Inventors: Denis Drapeau, Salem, NH (US);
Jessica Snow, Sterling, MA (US);
Gregory Hiller, Wakefield, MA (US);
Yen Tung Luan, Chelmsford, MA (US)

(73) Assignee: Wyeth LLC, Madison, NJ (US)

(*) Notice: Subject to any disclaimer, the term of this patent is extended or adjusted under 35 U.S.C. 154(b) by 1176 days.

(21) Appl. No.: 12/040,392

(22) Filed: Feb. 29, 2008

(65) Prior Publication Data

US 2009/0068705 A1    Mar. 12, 2009

Related U.S. Application Data

(60) Provisional application No. 60/892,749, filed on Mar. 2, 2007.

(51) Int. Cl.
*C12P 21/04*    (2006.01)
*C12N 5/00*    (2006.01)

(52) U.S. Cl.
CPC .......... *C12N 5/0018* (2013.01); *C12N 2500/20* (2013.01); *C12N 2500/32* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,522,811 A | 6/1985 | Eppstein et al. | |
| 4,767,704 A | 8/1988 | Cleveland et al. | |
| 4,816,397 A | 3/1989 | Boss et al. | |
| 4,816,567 A | 3/1989 | Cabilly et al. | |
| 5,078,996 A | 1/1992 | Conlon et al. | |
| 5,166,320 A | 11/1992 | Wu et al. | |
| 5,549,892 A | 8/1996 | Friedman et al. | |
| 5,723,127 A | 3/1998 | Scott et al. | |
| 5,830,761 A | 11/1998 | Drapeau et al. | |
| 6,005,079 A | 12/1999 | Casterman et al. | |
| 6,015,695 A | 1/2000 | Casterman et al. | |
| 6,048,728 A | 4/2000 | Inlow et al. | |
| 6,103,529 A | 8/2000 | Price et al. | |
| 6,162,643 A | 12/2000 | Wille | |
| 6,765,087 B1 | 7/2004 | Casterman et al. | |
| 7,294,484 B2 | 11/2007 | Drapeau et al. | |
| 7,300,773 B2 | 11/2007 | Drapeau et al. | |
| 7,335,491 B2 | 2/2008 | Drapeau et al. | |
| 2004/0022792 A1 | 2/2004 | Klinke et al. | |
| 2004/0082764 A1 | 4/2004 | Kunz et al. | |
| 2005/0019859 A1* | 1/2005 | Schilling et al. | 435/69.1 |
| 2008/0081356 A1 | 4/2008 | Lasko et al. | |
| 2008/0108106 A1 | 5/2008 | Wang et al. | |

FOREIGN PATENT DOCUMENTS

| | | |
|---|---|---|
| EP | 117058 | 8/1984 |
| EP | 117060 | 8/1984 |
| EP | 171496 | 2/1986 |
| EP | 0173494 | 3/1986 |
| EP | 0239400 | 9/1987 |
| EP | 417563 | 3/1991 |
| EP | 4178014 | 3/1991 |
| GB | 2177096 B | 3/1986 |
| JP | 2007/075102 A | 3/2007 |
| WO | WO91/11172 | 8/1991 |
| WO | WO92/06193 | 4/1992 |
| WO | WO 92/13069 | 8/1992 |
| WO | WO94/02518 | 2/1994 |
| WO | WO98/17799 | 4/1998 |
| WO | WO 98/20734 | 5/1998 |
| WO | WO98/55148 | 12/1998 |
| WO | WO99/43839 | 9/1999 |
| WO | WO 00/18434 | 4/2000 |
| WO | WO 02/98368 | 6/2002 |
| WO | WO 02/098369 | 12/2002 |
| WO | WO-02/101019 A | 12/2002 |
| WO | WO 2004058944 | 7/2004 |
| WO | WO-2006/108455 A | 10/2006 |

OTHER PUBLICATIONS

Chaderjian et al. (Biotechnol. Prog. 2005, 21, 550-553).*
Altamirano et al. (Biotechnol. Prog. 2000, 16, 69-75).*
International Search Report, PCT/US2008/055447, date of mailing Jun. 4, 2008.
Written Opinion of the International Searching Authority, PCT/US2008/055447, date of mailing Jun. 4, 2008.
Bard et al. (2000) Nat. Med. 6:916-19, "*Peripherally administered antibodies against amyloid β-peptide enter the central nervous system and reduce pathology in a mouse model of Alzheimer disease*".
Berkner et al. (1988) BioTechniques 6:616, "*Development of Adenovirus Vectors for the Expression of Heterologous Genes*".
Capel et al. (1994) Immunomethods 4:25-34, "*Heterogeneity of Human IgG Fc Receptors*".
Chang et al. (1997) J. Clin. Invest., 100:4, "*Replacing the First Epidermal Growth Factor-like Domain of Factor IX with that of Factor VII Enhances Activity in Vitro and in Canine Hemophilia B*".
Chartier Harlan et al. (1991) Nature 353:844, "*Early-onset Alzheimer's disease caused by mutations at codon 717 of the β-amyloid precursor protein gene*".
Datta, R. et al. (1992) Proc. Natl. Acad. Sci. USA 89:10149-10153, "*Ionizing radiation activates transcription of the EGR1 gene via CArG elements*".

(Continued)

*Primary Examiner* — Suzanne M Noakes
*Assistant Examiner* — Jae W Lee

(57) ABSTRACT

An improved system for large scale production of polypeptides in cell culture is provided. In accordance with the present invention, cells expressing a polypeptide of interest are grown in media that contain copper, glutamate or both. The use of such a system allows production of polypeptides in which misfolding and/or aggregation are reduced, and in which total glycosylation is increased. Polypeptides expressed in accordance with the present invention may be advantageously used in the preparation of pharmaceutical, agricultural or other commercial compositions.

31 Claims, 10 Drawing Sheets

(56) References Cited

OTHER PUBLICATIONS de Haas et al. (1995) J. Lab. Clin. Med. 126:330-41, "Fcγ receptors of phagocytes".
DeVries et al. (1992) Science 255; 989-991, "The fms-like Tyrosine Kinase, a receptor for vascular endothelial growth factor".
Dodel et al. (2003) Lancet Neurology 2:215, "Immunotherapy for Alzheimer's Disease".
Drews (1996) Nature Biotechnology, 14:1516, "Genomic sciences and the medicine of tomorrow".
Duff et al. (1995) Nature 373:476-7, "Alzheimer's disease. Mouse model made".
Elliott et al. (2003) Nature Biotechnology 21(4):414-21, "Enhancement of the therapeutic protein in vivo activities through glycoengineering".
Flotte et al. (1992) Am. J. Respir. Cell Mol. Biol. 7:349-356, "Gene Expression from Adeno-associated Virus Vectors in Airway Epithelial Cells".
Flotte et al. (1993) J. Biol. Chem. 268:3781-3790, "Expression of the Cystic Fibrosis Transmembrane Conductance Regulator from a Novel Adeno-associated Virus Promoter".
Games et al. (1995) Nature 373:523, "Alzheimer-type neuropathology in transgenic mice overexpressing V717F β-amyloid precursor protein".
Gething et al. (1981) Nature, 293:620-625, "Cell-surface expression of influenza haemagglutin from a cloned DNA copy of the RNA gene".
Goate et al. (1991) Nature 349:704, Segregation of a missense mutation in the amyloid precursor protein gene with familial Alzheimer's disease.
Gorfien et al. (2003) Biopharm. International, 16(4):34-40 "Optimized Nutrient Additives for Fed-Batch Cultures".
Graham et al. (1977) J. Gen Virol., 36:59, Characteristics of a Human Cell Line Transformed by DNA from Human Adenovirus Type 5.
Graham and van der Erb (1973) Virology, 52:456-457, A New Technique for the Assay of Infectivity of Human Adenovirus 5 DNA.
Haj-Ahmand and Graham (1986) J. Virol. 57:267, "Development of a Helper-Independent Human Adenovirus Vector and its use in the Transfer of the Herpes Simplex Virus Thymidine Kinase Gene".
Hardy (1997) TINS 20: 154-159, "Amyloid, the presenilins and Alzheimer's disease".
Hermonat et al. (1984) Proc. Natl. Acad. Sci. USA 81:6466-6470, "Use of adeno-associated virus as a mammalian DNA cloning vector: Transduction of neomycin resistance into mammalian tissue culture cells".
Herz and Gerard (1993) Proc. Natl. Acad. Sci. USA, 90:2812-2816, April, "Adenovirus-mediated transfer of low density lipoprotein receptor gene acutely accelerates cholesterol clearance in normal mice".
Johnson-Wood et al. (1997) Proc. Natl. Acad. Sci. USA, 94:1550-1555, "Amyloid precursor protein processing and Aβ$_{42}$ deposition in a transgenic mouse model of Alzheimer disease".
Kaufman et al. (1987) EMBO J., 6:187-195, Translational efficency of polycistronic mRNAs and their utilization to express heterologous genes in mammalian cells.
Keown et al. (1990) Methods in Enzymology, 185:527-537, "Methods for Introducing DNA into Mammalian Cells".
Kozbor et al. (1983) Immunology Today, 4(3): 72-79, "The production of monoclonal antibodies from human lymphocytes".
Lao and Toth (1997) Biotechnology. Prog., 13(5): 688-691, "Effect of ammonium and lactate on growth and metabolism of a recombinant Chinese Hamster Ovary Cell Culture".
Lemarchand et al. (1992) Proc. Natl. Acad. Sci. USA, 89:6482-6486, "Adenovirus-mediated transfer of a recombinant human α$_1$-antitrypsin cDNA to human endothelial cells".
Lifely et al. (1995) Glycobiology, 5(8):813-822, "Glycosylation and biological activity of CAMPATH-1H expressed in different cell lines and grown under different culture conditions".
Mader, S. and White, J. H. (1993) Proc. Natl. Acad. Sci. USA, 90:5603-5607, "A steroid-inducible promoter for the controlled overexpression of cloned genes in eukaryotic cells".

Maloney et al. (2000) Journal of Biol. Chem., 275(13), "Mammalian Notch1 Is Modified with Two Unusual Forms of O-Linked Glycosylation Found on Epidermal Growth Factor-like Modules".
Manome, Y. et al. (1993) Biochemistry, 32(40):10607-10613, "Coinduction of c-jun gene expression and internucleosomal DNA fragmentation by ionizing radiation".
Mansour et al. (1988) Nature, 336:348-352, "Disruption of the proto-oncogene int-2 in mouse embryo-derived stem cells: a general strategy for targeting mutations to non-selectable genes".
Mantei et al. (1979) Nature, 281:40-46, "Rabbit β-globin mRNA production in mouse L cells transformed with cloned rabbit β-globin chromosomal DNA".
Mather (1980) Biol. Reprod., 23:243-252, "Establishment and Characterization of Two Distinct Mouse Testicular Epithelial Cell Lines".
Mather et al. (1982) Annals N.Y. Acad. Sci., 383:44-68, "Culture of testicular Cells in Hormone-Supplemented Serum-Free Medium".
McLaughlin et al. (1989) J. Virol., 62:1963-1973, "Adeno-Associated Virus General Transduction Vectors: Analysis of Proviral Structures".
Miller, A.D. (1990) Blood, 76:271-278, "Progress Toward Human Gene Therapy".
Milligan, G. and Rees, S. (1999) TIPS, 20:118-124, "Chimaeric Gα Proteins: their potential use in drug discovery".
Milstein et al. (1983) Nature, 305 (6):537-540, "Hybrid hybridomas and their use in immunohistochemistry".
Morrison et al. (1985) Proc. Natl. Acad. Sci. U.S.A., 81:6851-6855, "Chimeric human antibody molecules: Mouse antigen-binding domains with human constant region domains".
Mullan et al. (1992) Nature Genet., 1:345-347, "A pathogenic mutation for probable Alzheimer's disease in the APP gene at the N-terminus of β-amyloid".
Murrell et al. (1991) Science, 254:97-99, "A Mutation in the Amyloid Precursor Protein Associated with Hereditary Alzheimer's Disease".
Mustonen and Alitalo (1995) J. Cell Biol., 129:895-898, "Endothelial Receptor Tyrosine Kinases Involved in Angiogenesis".
Muzyczka et al. (1992) Curr. Topics in Micro. and Immunol., 158:97-129, "Use of Adeno-Associated Virus as a General Transduction Vector for Mammalian Cells".
Naismith and Sprang (1996) J. Inflamm., 47(1-2): 1-7, "Tumor Necrosis Factor Receptor Superfamily".
Okayama, et al. (1985) Mol. Cell Biol., 5:1136-1142, "Bacteriophage Lambda Vector for Transducing a cDNA Clone Library into Mammalian Cells".
Olsson et al. (1982) Meth. Enzymol., 92: 3-16, "Human-Human Monoclonal Antibody-Producing Hybridomas: Technical Aspects".
Przybylo et al. (2002) Cancer Cell International, 2(1):6, 1-5. "Different glycosylation of cadherins from human bladder non-malignant and cancer cell lines".
Quantin et al. (1992) Proc. Natl. Acad. Sci. USA, 89:2581-2584, "Adenovirus as an expression vector in muscle cell in vivo".
Ravetch and Kinet (1991) Annu. Rev. Immunol., 9:457-492, "Fc Receptors".
Rosenfeld et al. (1991) Science, 252:431-434, "Adenovirus-Mediated Transfer of a Recombinant α1-Antitrypsin Gene to the Lung Epithelium in vivo".
Rosenfeld et al. (1992) Cell, 68:143-155, In Vivo Transfer of the Human Cystic Fibrosis Transmembrane Conductance Regulator Gene to the Airway Epithelium.
Samulski et al. (1989) J. Virol., 63(9):3822-3828, "Helper-Free Stocks of Recombinant Adeno-Associated Viruses: Normal Integration Does Not Require Viral Gene Expression".
Sato et al. (1995) Nature, 376(6535):70-74, "Distinct Roles of the Receptor Tyrosine Kinases Tie-1 and Tie-2 in Blood Vessel Formation".
Schenk et al. (1999) Nature, 400:173-177, "Immunization with amyloid-β attenuates Alzheimer-disease-like pathology in the PDAPP mouse".
Seed, B. (1987) Nature, 329:840-842, "An LFA-3 cDNA encodes a phospholipid-linked membrane protein homologous to its receptor CD2".
Selkoe (1993) TINS, 16:403-409, "Physiological production of the β-amyloid protein and the mechanism of Alzheimer's disease".

(56) References Cited

OTHER PUBLICATIONS

Selkoe (1994) J. Neuropathol. Exp. Neurol., 53(5):438-447, *Alzheimer's Disease: A Central Role for Amyloid*.
Shibuya et al. (1990) Oncogene, 5:519-524, "*Nucleotide Sequence and Expression of a Novel Human receptor-type tyrosine kinase gene (flt) closely related to the fms family*".
Spencer, D. M. et al. (1993) Science, 262:1019-1024, "*Controlling Signal Transduction with Synthetic Ligands*".
Takeda et al. (1985) Nature, 314:452, "*Construction of Chimaeric Processed Immunoglobulin Genes Containing Mouse Variable and Human Constant Region Sequences*".
Teng et al. (1983) Proc. Natl. Acad. Sci. U.S.A., 80: 7308-7312, "*Construction and Testing of Mouse-Human Heteromyelomas for Human Monoclonal Antibody Production*".
Terman et al. (1991) Oncogene 6:1677-83, "*Identification of a New Endothelial Cell Growth Factor Receptor Tyrosine Kinase*".
Thomas, et al. (1987) Cell, 51:503-512, *Site-Directed Mutagenesis by Gene Targeting in Mouse Embryo-Derived Stem Cells*.
Tratschin et al. (1985) Mol. Cell. Biol., 5(11):3251-3260, "*Adeno-Associated Virus Vector for High-Frquency Integration, Expression, and Rescue of Genes in Mammalian Cells*".
Tratschin et al. (1985) Mol. Cell. Biol., 4(10):2072-2081, "*A Human Parvovirus, Adeno-Associated Virus, as a Eucaryotic Vector: Transient Expression and Encapsidation of the Procaryotic Gene for Chloramphenicol Acetyltransferase*".
Tratschin et al. (1984) J. Virol., 51(3):611-619, "*Genetic Analysis of Adeno-Associated Virus: Properties of Deletion Mutants Constructed in Vitro and Evidence for an Adeno-Associated Virus Replication Function*".
Staunton et al.,(1990) Cell, 61:243-254, "*The Arrangement of the Immunoglobulin-like Domains of ICAM-1 and the Binding Sited for the LFA-1 and Rhinovirus*".
Urlaub and Chasin, (1980) Proc. Natl. Acad. Sci. USA, 77(7):4216-4220 "*Isolation of Chinese Hamster Cell Mutants Deficient in Dihydrofolate Reductase Activity*".
Watson, S. and S. Arkinstall (1994) The G-Protein Linked Receptor Facts Book, Academic Press, San Diego Calif., pp. 130-132.
Wilson et al. (1992) J. Biol. Chem., 267(2):963-967, "*Hepatocyte-directed Gene Transfer in Vivo Leads to Transient Improvement of Hypercholesterolemia in Low Density Lipoprotein Receptor-deficient Rabbits*".
Wondisford et al. (1988) Mol. Endocrinol., 2:32-39, "*Cloning of the Human Thyrotropin β-Subunit Gene and Transient Expression of Biologically Active Human Thyrotropin after Gene Transfection*".
Wu, G. and Wu, C. H. (1988) J. Biol. Chem., 263(29):14621-14624, "*Receptor-mediated Gene Delivery and Expression in vivo*".
Yarden and Ullrich (1988) Ann. Rev. Biochem., 57:433-478, *Growth Factor Receptor Tyrosine Kinases*.
Hawley Nelson (2003), Current Protocols In Cell Biology 20.6.1.-20.6.1.7, *Transfection of Cultured Eukaryotic Cells Using Cationic Lipid Reagents*.

\* cited by examiner

*Integrated viable cell density (IVCD) of cell cultures grown under the experimental conditions described in Table 1.*

*Cumulative specific productivity (Qp) of cell cultures grown under the experimental conditions described in Table 1.*

Day 10 relative of misfolded and/or aggregated produced TNFR-Ig and the Day 10 titer of cell cultures grown under the experimental conditions described in Table 1.

Integrated viable cell density (IVCD) of cell cultures grown under the experimental conditions described in Table 2.

USE OF COPPER AND GLUTAMATE IN CELL CULTURE FOR PRODUCTION OF POLYPEPTIDES

CROSS REFERENCE TO RELATED APPLICATIONS

This application is copending with, shares at least one common inventor with, and claims priority to U.S. Provisional Patent Application No. 60/892,749 filed Mar. 2, 2007, the entire contents of which are hereby incorporated by reference.

BACKGROUND

Proteins and polypeptides have become increasingly important therapeutic agents. In most cases, these proteins and polypeptides are produced in cell culture, from cells that have been engineered and/or selected to produce unusually high levels of the particular protein or polypeptide of interest. Control and optimization of cell culture conditions is important for successful commercial production of proteins and polypeptides.

Many proteins and polypeptides produced in cell culture are made in a batch or fed-batch process, in which cells are cultured for a period of time, and then the culture is terminated and the produced protein or polypeptide is isolated. Alternatively, proteins or polypeptides can be produced in a perfusion cell culture process in which the culture is not terminated and new nutrients and other components are periodically or continuously added to the culture, and during which the expressed protein or polypeptide is periodically or continuously harvested. The ultimate amount and quality of protein or polypeptide produced can be dramatically affected by the conditions of the cell culture. For example, traditional batch and fed-batch culture processes often result in proteins and polypeptides that are misfolded and/or are in the form of aggregates. Increased levels of misfolded and/or aggregated proteins or polypeptides tend to lead to lower overall yields of correctly folded and/or non-aggregated proteins or polypeptides. Furthermore, traditional batch and fed-batch culture processes often result in proteins or polypeptides with less extensive or otherwise undesirable glycosylation patterns.

A system for producing proteins or polypeptides that fold correctly, aggregate less readily or have a more desirable glycosylation pattern could potentially result in a therapeutic protein or polypeptide agent with greater potency and fewer side effects. Furthermore, such proteins or polypeptides could serve as more effective agricultural or other commercial agents. There thus exists a need for improved systems and compositions that result in a production of a protein or polypeptide that folds correctly, aggregates less and/or has a more desirable glycosylation pattern. There is a particular need for the development of improved systems for producing proteins or polypeptides in a cell culture grown in defined media.

SUMMARY

The present invention provides improved systems for large scale production of proteins and/or polypeptides in cell culture. In certain embodiments, the present invention provides a system for producing a protein or polypeptide in a cell culture medium comprising copper. In certain embodiments, the present invention provides a system for producing a protein or polypeptide in a cell culture medium comprising glutamate. In some embodiments, the present invention provides a system for producing a protein or polypeptide in a cell culture medium comprising both copper and glutamate. In certain embodiments, cell culture media of the present invention are used to grow mammalian cells that express a protein or polypeptide of interest.

In certain embodiments, the present invention provides commercial scale (e.g., 500 L or more) culture methods that utilize a medium containing copper and/or glutamate. In certain embodiments, the culture methods as taught in the present disclosure include one or more temperature shifts during the course of the cell culture. According to certain aspects of the present invention, use of such methods results in higher levels of correctly folded protein polypeptide than would be observed in a polypeptide grown in an otherwise identical medium under otherwise identical growth conditions. Furthermore, according to some aspects of the present invention, use of such methods results in production of a polypeptide with a more extensive or otherwise more desirable glycosylation pattern than would be observed in a polypeptide grown in an otherwise identical medium under otherwise identical growth conditions. In certain embodiments, use of such methods results in a production of a polypeptide with an increase of total sialylation than would be observed in a polypeptide grown in an otherwise identical medium under otherwise identical growth conditions.

One of ordinary skill in the art will understand that media formulations of the present invention encompass both defined and complex media. In certain embodiments, the culture medium is a defined medium in which the composition of the medium is known and controlled.

In some embodiments, the cells are grown under one or more of the conditions described in U.S. patent application Ser. Nos. 11/213,308, 11/213,317 and 11/213,633, each of was filed Aug. 25, 2005, and each of which is incorporated herein by reference in its entirety. In some embodiments, the cells are grown under one or more of the conditions described in U.S. Provisional Patent Application Ser. No. 60/830,658, filed Jul. 13, 2006 and incorporated herein by reference in its entirety. In some embodiments, the cells are grown under one or more of the conditions described in U.S. Provisional Patent Application Ser. No. 60/856,615, filed Nov. 3, 2006 and incorporated herein by reference in its entirety.

Cell cultures of the present invention may optionally be supplemented with nutrients and/or other medium components including for example hormones and/or other growth factors, ions (such as sodium, chloride, calcium, magnesium, and/or phosphate), buffers, vitamins, nucleosides or nucleotides, trace elements (inorganic compounds usually present at very low final concentrations), amino acids, lipids, and/or glucose or other energy sources. In certain embodiments, it may be beneficial to supplement the media with one or more chemical inductants such as hexamethylene-bis(acetamide) ("HMBA") and sodium butyrate ("NaB"). These optional supplements may be added at the beginning of the culture or may be added at a later point in order to replenish depleted nutrients or for another reason. In certain embodiments, it is desirable to select the initial medium composition to minimize supplementation in accordance with the present invention.

In certain embodiments, the total time a given cell culture is allowed to proceed is significantly increased beyond traditional culture times, thereby increasing the yield and quality of any given polypeptide produced in the cell culture and providing increased flexibility to the practitioner to determine

DEFINITIONS

Figure 1:
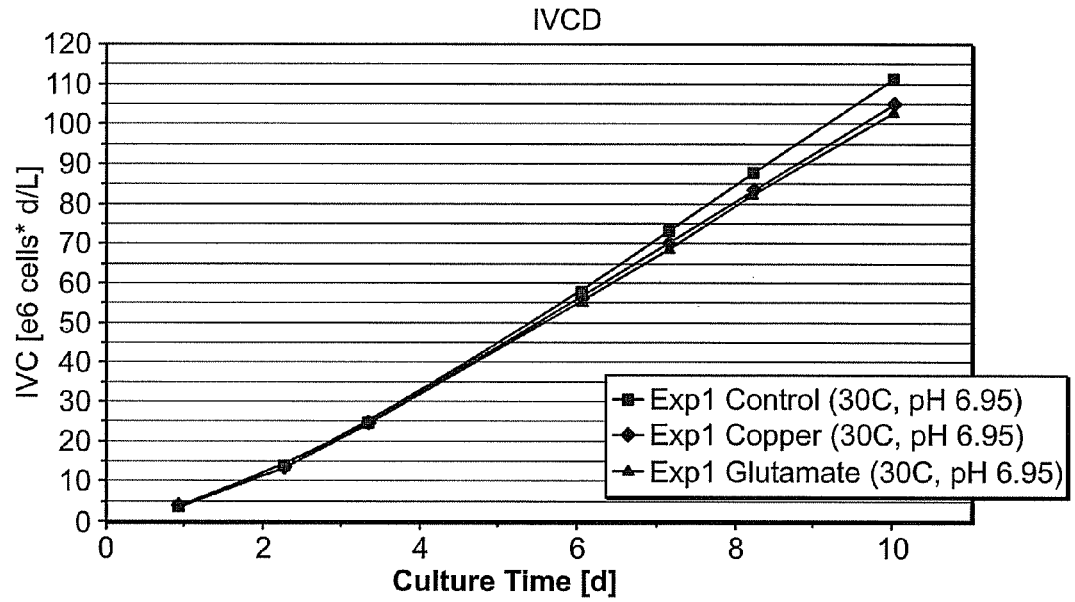
FIG. 1 shows the integrated viable cell density (IVCD) of cell cultures grown under the experimental conditions described in Table 3.

"Amino acid": The term "amino acid" as used herein refers to any of the twenty naturally occurring amino acids that are normally used in the formation of polypeptides, analogs or derivatives of those amino acids or any non-naturally occurring amino acid. In certain embodiments, amino acids of the present invention are provided in medium to cell cultures. The amino acids provided in the medium may be provided as salts or in hydrate form.

"Antibody": The term "antibody" as used herein refers to an immunoglobulin molecule or an immunologically active portion of an immunoglobulin molecule, i.e., a molecule that contains an antigen binding site which specifically binds (immunoreacts with) an antigen, such as a Fab or F(ab')$_2$ fragment. In certain embodiments, the antibody is a typical natural antibody known to those of ordinary skill in the art, e.g., glycoprotein comprising four polypeptide chains: two heavy chains and two light chains. In certain embodiments, the antibody is a single-chain antibody. For example, in some embodiments, the single-chain antibody comprises a variant of a typical natural antibody wherein two or more members of the heavy and/or light chains have been covalently linked, e.g., through a peptide bond. In certain embodiments, the single-chain antibody is a protein having a two-polypeptide chain structure consisting of a heavy and a light chain, which chains are stabilized, for example, by interchain peptide linkers, which protein has the ability to specifically bind an antigen. In certain embodiments, the antibody is an antibody comprised only of heavy chains such as, for example, those found naturally in members of the Camelidae family, including llamas and camels (see, for example, U.S. Pat. No. 6,765, 087 by Casterman et al., U.S. Pat. No. 6,015,695 by Casterman et al., U.S. Pat. No. 6,005,079 and by Casterman et al., each of which is incorporated by reference in its entirety). The terms "monoclonal antibodies" and "monoclonal antibody composition", as used herein, refer to a population of antibody molecules that contain only one species of an antigen binding site and therefore usually interact with only a single epitope or a particular antigen. Monoclonal antibody compositions thus typically display a single binding affinity for a particular epitope with which they immunoreact. In certain embodiments, a monoclonal antibody is a humanized antibody, wherein the large majority of the amino acid residues are derived from human antibodies, thus minimizing any potential immune reaction when delivered to a human subject. The terms "polyclonal antibodies" and "polyclonal antibody composition" refer to populations of antibody molecules that contain multiple species of antigen binding sites that interact with a particular antigen.

"Batch culture": The term "batch culture" as used herein refers to a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

"Bioreactor": The term "bioreactor" as used herein refers to any vessel useful for the growth of a cell culture. The bioreactor can be of any size so long as it is useful for the culturing of cells. In certain embodiments, such cells are mammalian cells. Typically, the bioreactor will be at least 1 liter and may be 10, 100, 250, 500, 1,000, 2,500, 5,000, 8,000, 10,000, 12,000 liters or more, or any volume in between. The internal conditions of the bioreactor, including, but not limited to pH and temperature, are optionally controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or glycoprotein of interest. The volume of the production bioreactor is typically at least 500 liters and may be 1,000, 2,500, 5,000, 8,000, 10,000, 12,000 liters or more, or any volume in between. One of ordinary skill in the art will be aware of and will be able to choose suitable bioreactors for use in practicing the present invention.

"Cell density": The term "cell density" as used herein refers to that number of cells present in a given volume of medium.

"Cell viability": The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

"Complex medium": The term "complex medium" as used herein refers to a medium that contains at least one component whose identity or quantity is either unknown or uncontrolled.

"Culture", "Cell culture": These terms as used herein refer to a cell population that is suspended in a medium (see definition of "medium" below) under conditions suitable to survival and/or growth of the cell population. As will be clear from context to those of ordinary skill in the art, these terms as used herein also refer to the combination comprising the cell population and the medium in which the population is suspended. In certain embodiments, the cell culture is a mammalian cell culture.

"Defined medium": The term "defined medium" as used herein refers to a medium in which the composition of the medium is both known and controlled.

"Fed-batch culture": The term "fed-batch culture" as used herein refers to a method of culturing cells in which additional components are provided to the culture at some time subsequent to the beginning of the culture process. The provided components typically comprise nutritional components for the cells which have been depleted during the culturing process. Additionally or alternatively, such additional components may include supplementary components (see definition of "Supplementary components" below). In certain embodiments, such additional components are provided in a feed medium (see definition of "Feed medium" below). A fed-batch culture is typically stopped at some point and the cells and/or components in the medium are harvested and optionally purified.

"Feed medium": The term "feed medium" as used herein refers to a solution containing nutrients that nourish growing mammalian cells that is added after the beginning of the cell culture. A feed medium may contain components identical to those provided in the initial cell culture medium. Additionally or alternatively, a feed medium may contain one or more additional components beyond those provided in the initial cell culture medium. Additionally or alternatively, a feed medium may lack one or more components that were provided in the initial cell culture medium. In certain embodiments, one or more components of a feed medium are provided at concentrations or levels identical or similar to the concentrations or levels at which those components were provided in the initial cell culture medium. In certain embodiments, one or more components of a feed medium are provided at concentrations or levels different than the concentrations or levels at which those components were provided in the initial cell culture medium. Exemplary feed media are shown in Table 2, although the present invention is not limited to the use of these media. One of ordinary skill in the art will recognize that alternative feed media may be used and/or certain alterations may be made to the compositions of the exemplary feed media listed in Table 2. In certain embodiments, a feed medium contains supplementary components (see definition of "Supplementary components" below).

"Fragment": The term "fragment" as used herein refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In certain embodiments, the fraction of activity retained is at least 10% of the activity of the full-length polypeptide. In certain embodiments, the fraction of activity retained is at least 20%, 30%, 40%, 50%, 60%, 70%, 80% or 90% of the activity of the full-length polypeptide. In certain embodiments, the fraction of activity retained is at least 95%, 96%, 97%, 98% or 99% of the activity of the full-length polypeptide. In certain embodiments, the fraction of activity retained is 100% or more of the activity of the full-length polypeptide. Alternatively or additionally, the term as used herein also refers to any portion of a given polypeptide that includes at least an established sequence element found in the full-length polypeptide. In some embodiments, the sequence element spans at least 4-5, 10, 15, 20, 25, 30, 35, 40, 45, 50 or more amino acids of the full-length polypeptide.

"Gene": The term "gene" as used herein refers to any nucleotide sequence, DNA or RNA, at least some portion of which encodes a discrete final product, typically, but not limited to, a polypeptide. Optionally, the term refers not only to the coding sequence that encodes the polypeptide or other discrete final product, but may also encompass regions preceding and/or following the coding sequence that modulate the basal level of expression (see definition of "genetic control element" below), as well as intervening sequences ("introns") between individual coding segments ("exons").

"Genetic control element": The term "genetic control element" as used herein refers to any sequence element that modulates the expression of a gene to which it is operably linked. Genetic control elements may function by either increasing or decreasing the expression levels and may be located before, within or after the coding sequence. Genetic control elements may act at any stage of gene expression by regulating, for example, initiation, elongation or termination of transcription, mRNA splicing, mRNA editing, mRNA stability, mRNA localization within the cell, initiation, elongation or termination of translation, or any other stage of gene expression. Genetic control elements may function individually or in combination with one another.

"Glycoprotein": The term "glycoprotein" as used herein refers to a protein or polypeptide that contains one or more covalently linked oligosaccharide chains. The oligosaccharide chains may be composed of a single sugar residue, a single unbranched chain of sugar residues or a chain of sugar residues that branches one or more times. The oligosaccharide chains may be either N-linked or O-linked.

"Glycosylation pattern": The term "glycosylation pattern" refers to the observed glycosylation of a given glycoprotein or glycoproteins. A glycoprotein with a greater number of covalently linked sugar residues in its oligosaccharide chain(s) is said to have an increased or more extensive glycosylation pattern. Conversely, a glycoprotein with fewer covalently linked sugar residues in its oligosaccharide chain(s) is said to have a decreased or less extensive glycosylation pattern. The term "glycosylation pattern" as used herein also refers to a characteristic distribution of several different glycosylation patterns on individual glycoproteins expressed according to the teachings of the present invention. In this sense, an increased glycosylation pattern refers to an increase in the characteristic distribution of glycosylation patterns of the expressed glycoproteins.

"Host cell": The term "host cell" as used herein refers to a cell that is grown in culture according to the present invention to produce a protein or polypeptide of interest. The term also refers to a cell that is manipulated according to the present invention to produce a glycoprotein. In certain embodiments, the glycoprotein produced in the host cell exhibits a more extensive and/or a more desirable glycosylation pattern when produced according to methods and in compositions as described herein. In certain embodiments, the host cell is a mammalian cell.

"Hybridoma": The term "hybridoma" as used herein refers to a cell or progeny of a cell resulting from fusion of an immortalized cell and an antibody-producing cell. The resulting hybridoma is an immortalized cell that produces antibodies. The individual cells used to create the hybridoma can be from any mammalian source, including, but not limited to, rat, pig, rabbit, sheep, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., *Nature*, 537:3053, 1983).

"Integrated Viable Cell Density", "IVCD": The terms "integrated viable cell density" or "IVCD" as used herein refer to the average density of viable cells over the course of the culture multiplied by the amount of time the culture has run. When the amount of polypeptide and/or protein produced is proportional to the number of viable cells present over the course of the culture, integrated viable cell density is a useful tool for estimating the amount of polypeptide and/or protein produced over the course of the culture.

"Medium", "Cell culture medium", "Culture medium": These terms as used herein refer to a solution containing nutrients that nourish growing cells. In certain embodiments, the culture medium is useful for growing mammalian cells. Typically, a culture medium provides essential and non-essential amino acids, vitamins, energy sources, lipids, and trace elements required by the cell for minimal growth and/or survival. A culture medium may also contain supplementary components (see definition of "Supplementary components" below) that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In certain embodiments, a medium is advantageously formulated to a pH and salt concentration optimal for cell survival and proliferation. Exemplary culture media are shown in Table 1, although the present invention is not limited to the use of these media. One of ordinary skill in the art will recognize that alternative culture media may be used and/or certain alterations may be made to the compositions of the exemplary culture media listed in Table 1. In certain embodiments, the medium is a feed medium that is added after the beginning of the cell culture (see definition of "Feed medium", above). In certain embodiments, the cell culture medium is a mixture of a starting nutrient solution and any feed medium that is added after the beginning of the cell culture.

"Metabolic waste product": The term "metabolic waste product" as used herein refers to a compound produced by a cell culture as a result of normal or non-normal metabolic processes that are in some way detrimental to the cell culture, particularly in relation to the expression or activity of a desired recombinant polypeptide or protein. For example, the metabolic waste products may be detrimental to the growth or viability of the cell culture, may decrease the amount of recombinant polypeptide or protein produced, may alter the folding, stability, aggregation, glycoslyation or other post-translational modification of the expressed polypeptide or protein, or may be detrimental to the cells and/or expression or activity of the recombinant polypeptide or protein in any number of other ways. Exemplary metabolic waste products include lactate, which is produced as a result of glucose metabolism, and ammonium, which is produced as a result of glutamine metabolism. A cell culture may produce one or more than one metabolic waste products.

"Polypeptide": The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. For example, a polypeptide may be glycosylated (see definition of "glycoprotein" above).

"Protein": The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of multiple polypeptides that physically associate with one another, the term "protein" as used herein refers to the multiple polypeptides that are physically coupled and function together as the discrete unit.

"Recombinantly expressed polypeptide" and "Recombinant polypeptide": These terms as used herein refer to a polypeptide expressed from a host cell that has been manipulated by the hand of man to express that polypeptide. In certain embodiments, the host cell is a mammalian cell. In certain embodiments, this manipulation may comprise one or more genetic modifications. For example, the host cells may be genetically modified by the introduction of one or more heterologous genes encoding the polypeptide to be expressed. The heterologous recombinantly expressed polypeptide can be identical or similar to polypeptides that are normally expressed in the host cell. The heterologous recombinantly expressed polypeptide can also be foreign to the host cell, e.g. heterologous to polypeptides normally expressed in the host cell. In certain embodiments, the heterologous recombinantly expressed polypeptide is chimeric. For example, portions of a polypeptide may contain amino acid sequences that are identical or similar to polypeptides normally expressed in the host cell, while other portions contain amino acid sequences that are foreign to the host cell. Additionally or alternatively, a polypeptide may contain amino acid sequences from two or more different polypeptides that are both normally expressed in the host cell. Furthermore, a polypeptide may contain amino acid sequences from two or more polypeptides that are both foreign to the host cell. In some embodiments, the host cell is genetically modified by the activation or upregulation of one or more endogenous genes.

"Supplementary components": The term "supplementary components" as used herein refers to components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In certain embodiments, supplementary components are added to the initial cell culture. In certain embodiments, supplementary components are added after the beginning of the cell culture.

"Titer": The term "titer" as used herein refers to the total amount of recombinantly expressed protein or polypeptide produced by a mammalian cell culture in a given amount of medium volume. Titer is typically expressed in units of milligrams of protein or polypeptide per milliliter of medium.

DETAILED DESCRIPTION OF CERTAIN EMBODIMENTS

The present invention provides improved systems and media formulations for the production of proteins and/or polypeptides by cell culture. In certain embodiments, the invention provides systems that minimize misfolded and/or aggregated protein products. When misfolded or aggregated proteins or polypeptides are produced, the total amount of desirable protein or polypeptide produced in a cell culture is thereby decreased. According to certain embodiments, the reduction or elimination of misfolded and/or aggregated proteins or polypeptides is achieved through the use of methods comprising providing a cell culture comprising copper. In some embodiments, the reduction or elimination of misfolded and/or aggregated proteins or polypeptides is achieved through the use of methods comprising providing a cell culture comprising glutamate. In certain embodiments, the reduction or elimination of misfolded and/or aggregated proteins or polypeptides is achieved through the use of methods comprising providing a cell culture comprising both copper and glutamate.

Certain methods of the present invention also include increasing the total amount of glycosylation, or otherwise producing a more desirable glycosylation pattern, in a protein or polypeptide produced in cell culture. In certain embodiments, increasing the total amount of glycosylation, or otherwise producing a more desirable glycosylation pattern, in a produced protein or polypeptide is achieved through the use of methods comprising providing a cell culture comprising copper. In some embodiments, increasing the total amount of glycosylation, or otherwise producing a more desirable glycosylation pattern, in a produced protein or polypeptide is achieved through the use of methods comprising providing a cell culture comprising glutamate. In some embodiments, increasing the total amount of glycosylation, or otherwise producing a more desirable glycosylation pattern, in a produced protein or polypeptide is achieved through the use of methods comprising providing a cell culture comprising both copper and glutamate. In certain embodiments, the cell culture is a batch or fed-batch culture.

Certain compositions of the present invention include a cell culture medium comprising copper. Certain compositions of the present invention include a cell culture medium comprising glutamate. Certain compositions of the present invention include a cell culture medium comprising both copper and glutamate. According to some embodiments, the fraction of misfolded and/or aggregated polypeptide grown in inventive media compositions, relative to the total polypeptide produced, is decreased compared to the fraction of misfolded and/or aggregated polypeptide that would be observed if the cells were grown in an otherwise identical medium that lacks copper and/or glutamate. Furthermore, in some embodiments, the total sialylation of polypeptides produced by cells grown in inventive media compositions is increased relative to the total sialylation of a peptide produced by cells grown in an otherwise identical medium that lacks copper and/or glutamate.

Certain embodiments and aspects are discussed in detail below. Those of ordinary skill in the art will understand, however, that various modifications to these embodiments are within the scope of the appended claims. It is the claims and equivalents thereof that define the scope of the present invention, which is not and should not be limited to or by this description of certain embodiments.

Cells

Any host cell susceptible to cell culture, and to expression of proteins or polypeptides, may be utilized in accordance with the present invention. In certain embodiments, the host cell is mammalian. Non-limiting examples of mammalian cells that may be used in accordance with the present invention include BALB/c mouse myeloma line (NSO/l, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (WI138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

As noted above, in many instances the cells will be selected or engineered to produce high levels of a protein or polypeptide of interest. Often, cells are manipulated to produce high levels of protein, for example by introduction of a gene encoding the protein or polypeptide of interest and/or by introduction of control elements that regulate expression of the gene (whether endogenous or introduced) encoding the protein or polypeptide of interest.

One of ordinary skill in the art will appreciate that proteins or polypeptides produced in different cell types may contain different resulting glycosylation patterns. For example, Przybylo et al. demonstrated that the glycosylation patterns of cadherins differed when expressed in non-malignant epithelial ureter cells, v-raf transfected HCV29 cells and transitional cell cancers of the urinary bladder (see Przybylo et al., Cancer Cell International, 2(1):6, 2002). Lifely et al. demonstrated that the glycosylation pattern and biological activity of a humanized IgG antibody differed when expressed in CHO, Y0 myeloma and NS0 myeloma cell lines (see Lifely et al., Glycobiology, 5(8):813-22, 1995). Methods of detecting and measuring the extent and pattern of glycoslyation of a particular protein or polypeptide are known in the art. Thus, one of ordinary skill in the art will be able to select the most desirable cell line for production of any given protein or polypeptide without undue experimentation. Regardless of which cell line is ultimately selected, methods and compositions of the present invention may be used to produce a protein or polypeptide with a more extensive or otherwise more desirable glycosylation pattern.

Certain polypeptides may have detrimental effects on cell growth, cell viability or some other characteristic of the cells that ultimately limits production of the polypeptide or protein of interest in some way. Even amongst a population of cells of one particular type engineered to express a specific polypeptide, variability within the cellular population may exist such that certain individual cells will grow better, produce more polypeptide of interest, produce a polypeptide that is less prone to misfolding and/or aggregation, and/or produce a polypeptide with a more extensive or otherwise more desirable glycosylation pattern. In certain embodiments, the cell line is empirically selected by the practitioner for robust growth under the particular conditions chosen for culturing the cells. In certain embodiments, individual cells engineered to express a particular polypeptide are chosen for large-scale production based on cell growth, final cell density, percent cell viability, titer of the expressed polypeptide, correct folding, a desirable glycosylation pattern or any combination of these or any other conditions deemed important by the practitioner.

Culturing the Cells

The present invention may be used with any cell culture method or system that is amenable to the expression of polypeptides. For example, the cells may be grown in batch or fed-batch cultures, where the culture is terminated after sufficient expression of the polypeptide, after which the expressed polypeptide is harvested and optionally purified. Alternatively, the cells may be grown in perfusion cultures, where the culture is not terminated and new nutrients and other components are periodically or continuously added to the culture, during which the expressed polypeptide is periodically or continuously harvested.

The cells may be grown in any convenient volume chosen by the practitioner. For example, the cells may be grown in small scale reaction vessels ranging in volume from a few milliliters to several liters. Alternatively, the cells may be grown in large scale commercial Bioreactors ranging in volume from approximately least 1 liter to 10, 100, 250, 500, 1000, 2500, 5000, 8000, 10,000, 12,000 liters or more, or any volume in between The temperature of the cell culture will be selected based primarily on the range of temperatures at which the cell culture remains viable, at which a high level of polypeptide is produced, at which misfolding and/or aggregation of the polypeptide are reduced, at which the polypeptide exhibits a more extensive or otherwise more desirable glycosylation pattern, or any combination of these or other factors deemed important by the practitioner. For example, CHO cells grow well and produce high levels or protein or polypeptide and/or produce glycoproteins with desirable glycosylation patterns at approximately 37° C. In general, most mammalian cells grow well and can produce high levels or protein or polypeptide and/or produce glycoproteins with desirable glycosylation patterns within a range of about 25° C. to 42° C., although methods taught by the present disclosure are not limited to these temperatures. Certain mammalian cells grow well and can produce high levels or protein or polypeptide and/or produce glycoproteins with desirable glycosylation patterns within the range of about 35° C. to 40° C. In certain embodiments, the cell culture is grown at a temperature of 20, 21, 22, 23, 24, 25, 26, 27, 28, 29, 30, 31, 32, 33, 34, 35, 36, 37, 38, 39, 40, 41, 42, 43, 44, or 45° C. at one or more times during the cell culture process. Those of ordinary skill in the art will be able to select appropriate temperature or temperatures in which to grow cells, depending on the needs of the cells and the production requirements of the practitioner.

Furthermore, the culture may be subjected to one or more temperature shifts during the course of the culture. When shifting the temperature of the culture, the temperature shift may be relatively gradual. For example, it may take several hours or days to complete the temperature change. Alternatively, the temperature shift may be relatively abrupt. The temperature may be steadily increased or decreased during the culture process. Additionally or alternatively, the temperature may be increased or decreased by discrete amounts at various times during the culture process. The subsequent temperature(s) or temperature range(s) may be lower than or higher than the initial or previous temperature(s) or temperature range(s). One of ordinary skill in the art will understand that multiple temperature shifts are encompassed by the present invention. For example, the temperature may be shifted once (either to a higher or lower temperature or temperature range), the cells maintained at this temperature or temperature range for a certain period of time, after which the temperature may be shifted again to a new temperature or temperature range, which may be either higher or lower than the temperature or temperature range of the previous temperature or temperature range. The temperature of the culture after each discrete shift may be constant or may be maintained within a certain range of temperatures.

As with the initial temperature or temperature range, the temperature or temperature range of the cell culture after the temperature shift(s) is generally selected based primarily on the temperature(s) at which the cell culture remains viable, the range in which a high level of glycoprotein is produced and/or the range in which the expressed glycoprotein contains a desirable glycosylation pattern. In general, most mammalian cells remain viable and express glycoproteins with desirable glycosylation patterns at commercially adequate levels within a range of about 25° C. to 42° C., although methods taught by the present disclosure are not limited to these temperatures. In certain embodiments, mammalian cells remain viable and express glycoproteins with desirable glycosylation patterns at commercially adequate levels within a range of about 25° C. to 35° C. In certain embodiments, the cell culture is grown at a temperature of 20, 21, 22, 23, 24, 25, 26, 27, 28, 29, 30, 31, 32, 33, 34, 35, 36, 37, 38, 39, 40, 41, 42, 43, 44, or 45° C. at one or more times after the temperature shift(s). Those of ordinary skill in the art will be able to select appropriate temperature(s) or temperature range(s) in which to grow cells after the temperature shift(s), depending on the particular needs of the cells and the particular production requirements of the practitioner. The cells may be grown for any amount of time, depending on the needs of the practitioner and the requirement of the cells themselves.

In certain embodiments, batch and/or fed-batch cell cultures are terminated once the expressed polypeptide reaches a sufficiently high titer. As non-limiting examples, cell cultures may be terminated when the polypeptide titer is 100, 200, 300, 400, 500, 600, 700, 800, 900, 1000, 1100, 1200, 1300, 1400, 1500, 2000 mg/L or higher. One of ordinary skill in the art will be able to select one or more appropriate titers at which a batch and/or fed-batch culture may be harvested. Additionally or alternatively, in certain embodiments, batch and/or fed-batch cell cultures are terminated once the expressed glycoprotein exhibits a desirable glycosylation pattern, as determined by the needs of the practitioner. Additionally and/or alternatively, batch and/or fed-batch cell cultures are terminated once the cells reach a sufficiently high density, as determined by the needs of the practitioner. For example, a culture may be terminated once the cells reach 1, 5, 10, 15, 20, 25, 30, 35, 40, 45, 50, 55, 60, 65, 70, 75, 80, 85, 90, 95 or 99 percent of maximal viable cell density. Additionally or alternatively, batch and/or fed-batch reactions may be terminated prior to excessive accumulation of metabolic waste products such as, for example, lactate and ammonium.

In certain embodiments, batch and/or fed-batch cell cultures are terminated to prevent the undesirable accumulation of misfolded and/or aggregated polypeptide. For example, cell cultures may be terminated when the relative fraction of misfolded and/or aggregated polypeptide is 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 percent of properly folded and/or non-aggregated polypeptide. In certain embodiments, cell cultures are terminated when the relative fraction of misfolded and/or aggregated polypeptide is less than one percent of properly folded and/or non-aggregated polypeptide. In certain embodiments, such a termination takes place well before a sufficiently high titer is achieved, before the cells reach a sufficiently high density and/or before metabolic waste products accumulate to excessive levels. In certain embodiments, cell cultures grown in accordance with methods and compositions of the present invention are able to grow for a longer period of time than would be possible using traditional culture methods since misfolding and/or aggregation of the produced polypeptide are reduced. For example, cells cultures grown in accordance with methods and compositions of the present invention may be grown for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days. One of ordinary skill in the art will appreciate that being able to grow cell cultures for a longer period of time with a reduced amount of misfolded and/or aggregated polypeptide will result in an increase in the amount of correctly folded, unaggregated polypeptide produced. Thus, certain methods and compositions of the present invention provide the practitioner added flexibility in determining the appropriate or optimal time to culture cells expressing a polypeptide of interest.

In certain cases, it may be beneficial or necessary to supplement the cell culture during the subsequent production phase with nutrients or other medium components that have been depleted or metabolized by the cells. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source. These supplementary components may all be added to the cell culture at one time, or they may be provided to the cell culture in a series of additions.

In certain embodiments, cells are grown in accordance with any of the cell culture methods described in U.S. patent application Ser. Nos. 11/213,308, 11/213,317 and 11/213,633 each of which was filed Aug. 25, 2005, and each of which is herein incorporated by reference in its entirety. For example, in certain embodiments, cells are grown in a culture medium in which the cumulative amino acid concentration is greater than about 70 mM. In certain embodiments, cells are grown in a culture medium in which the molar cumulative glutamine to cumulative asparagine ratio is less than about 2. In certain embodiments, cells are grown in a culture medium in which the molar cumulative glutamine to cumulative total amino acid ratio is less than about 0.2. In certain embodiments, cells are grown in a culture medium in which the molar cumulative inorganic ion to cumulative total amino acid ratio is between about 0.4 to 1. In certain embodiments, cells are grown in a culture medium in which the combined cumulative glutamine and cumulative asparagine concentration is between about 16 and 36 mM. In certain embodiments, cells are grown in a culture medium that contains two, three, four or all five of the preceding medium conditions. In certain embodiments, the concentration of glutamine in a cell culture medium is limited to less than approximately 13 mM. In certain embodiments, the concentration of glutamine in a cell culture medium is limited to less than approximately 4 mM.

In some embodiments, the cells are grown under one or more of the conditions described in U.S. Provisional Patent Application Ser. No. 60/830,658, filed Jul. 13, 2006 and incorporated herein by reference in its entirety. For example, in some embodiments, cells are grown in a culture medium that contains manganese at a concentration between approximately 10 and 600 nM. In some embodiments, cells are grown in a culture medium that contains manganese at a concentration between approximately 20 and 100 nM. In some embodiments, cells are grown in a culture medium that contains manganese at a concentration of approximately 40 nM.

In some embodiments, the cells are grown under one or more of the conditions described in U.S. Provisional Patent Application Ser. No. 60/856,615, filed Nov. 3, 2006 and incorporated herein by reference in its entirety. In some embodiments, cells are grown in a medium containing the glucose analog 2-deoxyglucose. In certain embodiments, a cell culture is grown in a medium containing 2-deoxyglucose, in which glutamine is present at a concentration that is less than approximately 13 mM. In certain embodiments, a cell culture is grown in a medium containing 2-deoxyglucose, in which glutamine is present at a concentration that is less than approximately 4 mM. In certain embodiments, a cell culture is grown in a medium containing di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl] trimethyl ammonium iodide, iodoacetate, and/or fluoroacetate, and optionally in which glutamine is present at a concentration that is less than approximately 13 mM or 4 mM.

One of ordinary skill in the art will be able to tailor specific cell culture conditions in order to optimize certain characteristics of the cell culture including but not limited to growth rate, cell viability, final cell density of the cell culture, final concentration of detrimental metabolic byproducts such as lactate and ammonium, final titer of the expressed polypeptide, reduction of misfolding and/or aggregation of the expressed polypeptide, a more extensive or otherwise more desirable glycosylation pattern of the expressed polypeptide or any combination of these or other conditions deemed important by the practitioner.

Media Compositions

Any of a wide variety of growth media may be used in accordance with the present invention. In certain embodiments, cells are grown in any of a variety of chemically defined media, wherein the components of the media are both known and controlled. In some embodiments, cells are grown in any of a variety of complex media, in which not all components of the medium are known and/or controlled.

Chemically defined growth media for cell culture have been extensively developed and published over the last several decades, including chemically defined growth media for mammalian cell culture. All components of defined media are well characterized, and so defined media do not contain complex additives such as serum or hydrolysates. Early media formulations were developed to permit cell growth and maintenance of viability with little or no concern for protein production or quality. More recently, media formulations have been developed with the express purpose of supporting highly productive cell cultures. However, much work remains to develop media formulations that result in a higher quality protein or polypeptide, for example, a protein or polypeptide that folds correctly, aggregates less and/or has a more extensive or otherwise more desirable glycosylation pattern.

Defined media typically consist of roughly fifty chemical entities at known concentrations in water. Most defined media also contain one or more well-characterized proteins such as insulin, IGF-1, transferrin or BSA, but others require no protein components and so are referred to as protein-free defined media. The chemical components of defined media generally fall into five broad categories: amino acids, vitamins, inorganic salts, trace elements, and a miscellaneous category that defies neat categorization.

All media, defined or complex, include an energy source for the growing cells. Often, the energy source is glucose, a simple monosaccharide sugar that has the chemical formula $C_6H_{12}O_6$. Traditional media formulations, including commercially available media such as Ham's F10 (Sigma), Minimal Essential Medium ([MEM], Sigma), RPMI-1640 (Sigma), and Dulbecco's Modified Eagle's Medium ([DMEM], Sigma), have contained relatively high levels of glucose. Glucose has traditionally been thought to be required in abundance since it is the primary metabolic energy sources for the cells. However, rapid consumption of glucose leads to the accumulation of lactate. Lactate is a detrimental metabolic waste product and is a known inhibitor of cell growth and productivity in cell culture (see Gorfien et al., Optimized Nutrient Additives for Fed-Batch Cultures, *Biopharm. International*, April 2003; Lao and Toth, Effect of ammonium and lactate on growth and metabolism of a recombinant Chinese Hamster Ovary Cell Culture, *Biotechnology. Prog.* 13(5): 688-691, 1997).

The present invention encompasses the finding that proteins or polypeptides produced by cell cultures grown in defined media using certain methods and compositions disclosed herein exhibit reduced polypeptide misfolding, reduced aggregation and/or a more extensive or otherwise more desirable glycosylation pattern than they otherwise would if the cells were grown in traditional media, such as those described above. In certain embodiments, media formulations comprising copper are useful in reducing misfolding and/or aggregation of produced polypeptides, or in producing a polypeptide with a more extensive or otherwise more desirable glycosylation pattern. For example, media formulations of the present invention may comprise copper at a concentration of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 15, 20, 25, 30, 35, 40, 45, 50, 55, 60, 65, 70, 75, 80, 85, 90, 95, or 100 µM.

In some embodiments, media formulations comprising glutamate are useful in reducing misfolding and/or aggregation of produced polypeptides, or in producing a polypeptide with a more extensive or otherwise more desirable glycosylation pattern. For example, media formulations of the present invention may comprise glutamate at a concentration of 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 mM.

One of ordinary skill in the art will understand that the foregoing concentrations of copper and/or glutamate in a cell culture medium may be achieved using a batch culture, a fed-batch culture, or a perfusion culture.

In certain embodiments, media formulations comprising both copper and glutamate are useful in reducing misfolding and/or aggregation of produced polypeptides, or in producing a polypeptide with a more extensive or otherwise more desirable glycosylation pattern.

Inventive media formulations disclosed herein may optionally be supplemented as necessary or desirable with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, protein hydrolysates, or glucose or other energy source. In certain embodiments of the present invention, it may be beneficial to supplement the media with chemical inductants such as hexamethylene-bis(acetamide) ("HMBA") and/or sodium butyrate ("NaB"). These optional supplements may be added at the beginning of the culture or may be added at a later point in order to replenish depleted nutrients or for another reason. One of ordinary skill in the art will be aware of any desirable or necessary supplements that may be included in media formulations of the present invention and will be able to select which particular supplements to add based on his or her experimental and/or other needs.

Polypeptides

Any polypeptide that is expressible in a host cell may be produced in accordance with the present invention. The polypeptide may be expressed from a gene that is endogenous to the host cell, or from a heterologous gene that is introduced into the host cell. The polypeptide may be one that occurs in nature, or may alternatively have a sequence that was engineered or selected by the hand of man. A polypeptide to be produced according to the present invention may be assembled from polypeptide fragments that individually occur in nature. Additionally or alternatively, the engineered polypeptide may include one or more fragments that are not naturally occurring.

Polypeptides that may desirably be expressed in accordance with the present invention will often be selected on the basis of an interesting or useful biological or chemical activity. For example, the present invention may be employed to express any pharmaceutically or commercially relevant enzyme, clotting factor, receptor, antibody, hormone, regulatory factor, antigen, binding agent, etc. The following list of polypeptides that can be produced according to the present invention is merely exemplary in nature, and is not intended to be a limiting recitation. One of ordinary skill in the art will understand that any polypeptide may be expressed in accordance with the present invention and will be able to select the particular polypeptide to be produced based on his or her particular needs.

Antibodies

Antibodies are proteins that have the ability to specifically bind a particular antigen. Given the large number of antibodies currently in use or under investigation as pharmaceutical or other commercial agents, production of antibodies in accordance with the present invention is of particular interest. For example, the present invention may be used to produce antibodies in a cell culture wherein the misfolding and/or aggregation of the produced antibodies are reduced.

Additionally or alternatively, the present invention may be used to produce antibodies in a cell culture wherein the produced antibodies have a more extensive or otherwise more desirable glycosylation pattern. Antibodies with differing glycosylation patterns may be less likely to initiate an immune response in the individual to which they are administered, resulting in a more effective therapeutic regimen. Additionally or alternatively, antibodies with differing glycosylation patterns in their constant regions may exhibit an improved pharmacokinetic or pharmacodynamic effector function. Additionally or alternatively, antibodies with differing glycosylation patterns may be more stable in the cell culture conditions in which they are produced, for example by being more resistant to proteases or other components in the cell culture, such that a higher final titer of antibody is produced.

Any antibody that can be expressed in a host cell may be used in accordance with the present invention. In some embodiments, the antibody to be expressed is a monoclonal antibody. In certain embodiments, the monoclonal antibody is a chimeric antibody. As in known in the art, a chimeric antibody contains amino acid fragments that are derived from more than one organism. Chimeric antibody molecules can include, for example, an antigen binding domain from an antibody of a mouse, rat, or other species, with human constant regions. A variety of approaches for making chimeric antibodies have been described. See e.g., Morrison et al., *Proc. Natl. Acad. Sci. U.S.A.* 81:6851, 1985; Takeda et al., *Nature* 314:452, 1985, Cabilly et al., U.S. Pat. No. 4,816,567; Boss et al. U.S. Pat. No. 4,816,397; Tanaguchi et al., European Patent Publication EP171496; European Patent Publication 0173494, United Kingdom Patent GB 2177096B, each of which is incorporated herein by reference in its entirety.

In certain embodiments, the monoclonal antibody is a humanized antibody. A humanized antibody is a chimeric antibody wherein the large majority of the amino acid residues are derived from human antibodies, thus minimizing any potential immune reaction when delivered to a human subject. In humanized antibodies, amino acid residues in the hypervariable region are replaced with residues from a non-human species that confer a desired antigen specificity or affinity. In certain embodiments, a humanized antibody has an amino acid sequence that is at least 80, 85, 90, 91, 92, 93, 94, 95, 96, 97, 98, 99 percent identical or higher to a human antibody. In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., *Proc. Natl. Acad. Sci. U.S.A.*, 80: 7308-7312, 1983; Kozbor et al., *Immunology Today*, 4: 7279, 1983; Olsson et al., *Meth. Enzymol.*, 92: 3-16, 1982), and may be made according to the teachings of PCT Publication WO92/06193 or EP 0239400, each of which is incorporated herein by reference in its entirety).

In certain embodiments, an antibody produced according to the teachings of the present disclosure contains an immunoglobulin constant or Fc region that exhibits an improved glycosylation pattern. For example, an antibody produced in accordance with the teachings herein may bind more strongly or with more specificity to effector molecules such as complement and/or Fc receptors, which can control several immune functions of the antibody such as effector cell activity, lysis, complement-mediated activity, antibody clearance, and antibody half-life. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, Annu. Rev. Immunol 9:457-92, 1991; Capel et al., Immunomethods 4:25-34, 1994; and de Haas et al., J. Lab. Clin. Med. 126:330-41, 1995, each of which is incorporated herein by reference in its entirety.

As but one non-limiting example, an antibody that may be produced according to the present teachings is an anti-ABeta antibody. Anti-ABeta antibodies are a particularly promising potential avenue of therapy in the treatment of Alzheimer's disease ("AD"). AD is a progressive disease resulting in senile dementia (see generally: Selkoe, TINS 16:403, 1993; Hardy et al., WO 92/13069; Selkoe, J. Neuropathol. Exp. Neurol. 53:438, 1994; Duff et al., Nature 373:476, 1995; Games et al., Nature 373:523, 1995, each of which is incorporated herein by reference). Broadly speaking, the disease falls into two categories: late onset, which occurs in old age (65+ years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 μm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed ABeta or Beta-amyloid peptide. ABeta peptide is a 4-kDa internal fragment of 39-43 amino acids of a larger transmembrane glycoprotein named protein termed amyloid precursor protein (APP). As a result of proteolytic processing of APP by different secretase enzymes, ABeta is primarily found in both a short form, 40 amino acids in length, and a long form, ranging from 42-43 amino acids in length. Part of the hydrophobic transmembrane domain of APP is found at the carboxy end of ABeta, and may account for the ability of ABeta to aggregate into plaques, particularly in the case of the long form. Accumulation of amyloid plaques in the brain eventually leads to neuronal cell death. The physical symptoms associated with this type of neural deterioration characterize Alzheimer's disease.

Several mutations within the APP protein have been correlated with the presence of AD (see, e.g., Goate et al., Nature 349:704, 1991 (valine717 to isoleucine); Chartier Harlan et al. Nature 353:844, 1991 (valine717 to glycine); Murrell et al., Science 254:97, 1991 (valine717 to phenylalanine); Mullan et al., Nature Genet. 1:345, 1992 (a double mutation changing lysine595-methionine596 to asparagine595-leucine596), each of which is incorporated herein by reference in its entirety). Such mutations are thought to cause AD by increased or altered processing of APP to ABeta, particularly processing of APP to increased amounts of the long form of ABeta (i.e., ABeta1-42 and ABeta1 43). Mutations in other genes, such as the presenilin genes, PS1 and PS2, are thought indirectly to affect processing of APP to generate increased amounts of long form ABeta (see Hardy, TINS 20: 154, 1997, incorporated herein by reference in its entirety).

Mouse models have been used successfully to determine the significance of amyloid plaques in AD (Games et al., supra; Johnson-Wood et al., Proc. Natl. Acad. Sci. USA 94:1550, 1997, incorporated herein by reference in its entirety). In particular, when PDAPP transgenic mice, (which express a mutant form of human APP and develop Alzheimer's disease at a young age), are injected with the long form of ABeta, they display both a decrease in the progression of Alzheimer's and an increase in antibody titers to the ABeta peptide (Schenk et al., Nature 400, 173, 1999, incorporated herein by reference in its entirety). The observations discussed above indicate that ABeta, particularly in its long form, is a causative element in Alzheimer's disease.

The ABeta peptide can exist in solution and can be detected in CNS (e.g., CSF) and plasma. Under certain conditions, soluble ABeta is transformed into fibrillary, toxic, Beta-sheet forms found in neuritic plaques and cerebral blood vessels of patients with AD. Treatments involving immunization with monoclonal antibodies against ABeta have been investigated. Both active and passive immunization have been tested as in mouse models of AD. Active immunization resulted in some reduction in plaque load in the brain, but only by nasal administration. Passive immunization of PDAPP transgenic mice has also been investigated (Bard, et al., Nat. Med. 6:916-19, 2000, incorporated herein by reference in its entirety). It was found that antibodies recognizing the amino-terminal and central domains of ABeta stimulated phagocytosis of ABeta deposits, whereas antibodies against domains near the carboxy-terminal domain did not.

The mechanism of clearance of ABeta after passive or active immunization is under continued investigation. Two mechanisms have been proposed for effective clearance, i.e., central degradation and peripheral degradation. The central degradation mechanism relies on antibodies being able to cross the blood-brain barrier, bind to plaques, and induce clearance of pre-existing plaques. Clearance has been shown to be promoted through an Fc-receptor-mediated phagocytosis (Bard, et al., supra). The peripheral degradation mechanism of ABeta clearance relies on a disruption of the dynamic equilibrium of ABeta between brain, CSF, and plasma upon administration of antibody, leading to transport of ABeta from one compartment to another. Centrally derived ABeta is transported into the CSF and the plasma where it is degraded. Recent studies have concluded that soluble and unbound ABeta are involved in the memory impairment associated with AD, even without reduction in amyloid deposition in the brain. Further studies are needed to determine the action and/or interplay of these pathways for ABeta clearance (Dodel, et al., The Lancet Vol. 2:215, 2003, incorporated herein by reference in its entirety).

Anti-ABeta antibodies are a potentially promising route of treatment of AD since they mat bind to and clear the ABeta or other components that comprise the amyloid plaques. Anti-ABeta antibodies produced in accordance with the teachings of the present disclosure may serve to better treat AD or other related diseases by, for example, binding and clearing components of amyloid plaques more effectively, by clearing amyloid plaques with fewer or less severe side effects, or by preventing formation or build-up of amyloid plaques. In certain embodiments, anti-ABeta antibodies produced in accordance with the present teachings are monoclonal antibodies.

In certain embodiments, anti-ABeta antibodies produced in accordance with the present teachings bind specifically to the aggregated form of ABeta without binding to the soluble form. In certain embodiments, anti-ABeta antibodies produced in accordance with the present teachings bind specifically to the soluble form of anti-ABeta under conditions at which they do not bind to the aggregated form. In certain embodiments, anti-ABeta antibodies produced in accordance with the present teachings bind to both aggregated and soluble forms. In certain embodiments, anti-ABeta antibodies produced in accordance with the present teachings bind ABeta in plaques. In certain embodiments, anti-ABeta antibodies produced in accordance with the present teachings cross the blood-brain barrier. In certain embodiments, anti-ABeta antibodies produced in accordance with the present teachings reduce amyloid burden in a subject. In certain embodiments, anti-ABeta antibodies produced in accordance with the present teachings reduce neuritic dystrophy in a subject. In certain embodiments, anti-ABeta antibodies can maintain synaptic architecture (e.g., synaptophysin).

According to some embodiments, anti-ABeta antibodies produced in accordance with the present teachings bind to an epitope within residues 13-28 of ABeta (with the first N terminal residue of natural ABeta designated 1). In some embodiments, anti-ABeta antibodies produced in accordance with the present teachings bind to an epitope within residues 19-22 of ABeta. In some embodiments, multiple monoclonal antibodies having binding specificities to different anti-ABeta epitopes are used. For example, in some embodiments, an antibody specific for an epitope within residues 19-22 of ABeta is co-administered with an antibody specific for an epitope outside of residues 19-22 of ABeta. Such antibodies can be administered sequentially or simultaneously. Antibodies to amyloid components other than ABeta can also be used (e.g., administered or co-administered).

In certain embodiments, anti-ABeta antibodies produced in accordance with the present teachings bind to an ABeta epitope more strongly or with more specificity than anti-ABeta antibodies otherwise produced. Epitope specificity of an antibody can be determined by known techniques, for example, by forming a phage display library in which different members display different subsequences of ABeta. The phage display library may then be selected for members specifically binding to an antibody under test. A family of sequences is isolated. Typically, such a family contains a common core sequence, and varying lengths of flanking sequences in different members. The shortest core sequence showing specific binding to the antibody typically defines the epitope bound by the antibody. Alternatively or additionally, antibodies may be tested for epitope specificity in a competition assay with an antibody whose epitope specificity has already been determined. For example, antibodies that compete with the 15C11 antibody for binding to ABeta are considered to bind to the same or similar epitope as 15C11, i.e., within residues ABeta 19-22. In certain embodiments, screening antibodies for epitope specificity is a useful predictor of therapeutic efficacy. For example, an antibody determined to bind to an epitope within residues 13-28 (e.g., to Aβ 19-22) of ABeta is likely to be effective in preventing and treating Alzheimer's disease according to the methodologies of the present invention.

Antibodies that specifically bind to a preferred segment of ABeta without binding to other regions of ABeta have a number of advantages relative to monoclonal antibodies binding to other regions, or to polyclonal sera to intact ABeta. Among other things, for equal mass dosages, dosages of antibodies that specifically bind to preferred segments contain a higher molar dosage of antibodies effective in clearing amyloid plaques. Also, antibodies specifically binding to preferred segments may induce a clearing response against amyloid deposits without inducing a clearing response against intact APP polypeptide, thereby reducing the potential side effects.

In certain embodiments, the monoclonal, chimeric, or humanized antibodies described above contain amino acid residues that do not naturally occur in any antibody in any species in nature. These foreign residues can be utilized, for example, to confer novel or modified specificity, affinity or effector function on the monoclonal, chimeric or humanized antibody.

Clotting Factors

Clotting factors have been shown to be effective as pharmaceutical and/or commercial agents. Hemophilia B is a disorder in which the blood of the sufferer is unable to clot. Thus, any small wound that results in bleeding is potentially a life-threatening event. Given the importance of recombinant clotting factors in the treatment of diseases such as hemophilia, production of clotting factors in accordance with the present invention is of particular interest. For example, the present invention may be used to produce clotting factors in a cell culture wherein the misfolding and/or aggregation of the produced clotting factors are reduced. Additionally or alternatively, the present invention may be used to produce clotting factors in a cell culture wherein the produced clotting factors have a more extensive or otherwise more desirable glycosylation pattern.

For example, Coagulation Factor IX (Factor IX or "FIX") is a single-chain glycoprotein whose deficiency results in Hemophilia B. FIX is synthesized as a single chain zymogen that can be activated to a two-chain serine protease (Factor IXa) by release of an activation peptide. The catalytic domain of Factor IXa is located in the heavy chain (see Chang et al., *J. Clin. Invest.*, 100:4, 1997, incorporated herein by reference in its entirety). FIX has multiple glycosylation sites including both N-linked and O-linked carbohydrates. One particular O-linked structure at Serine 61 (Sia-$\alpha$2,3-Gal-$\beta$1,4-GlcNAc-$\beta$1,3-Fuc-$\alpha$1-O-Ser) was once thought unique to FIX but has since found on a few other molecules including the Notch protein in mammals and Drosophila (Maloney et al, *Journal of Biol. Chem.*, 275(13), 2000). FIX produced by Chinese Hamster Ovary ("CHO") cells in cell culture exhibits some variability in the Serine 61 oligosaccharide chain. These different glycoforms, and other potential glycoforms, may have different abilities to induce clotting when administered to humans or animals and/or may have different stabilities in the blood, resulting in less effective clotting.

Hemophilia A, which is clinically indistinguishable from Hemophilia B, is caused by a defect in human clotting factor VIII, another glycoprotein that is synthesized as a single chain and then processed into a two-chain active form. The present invention may also be employed to control or alter the glycosylation pattern of clotting factor VIII in order to modulate its clotting activity. Other clotting factors that can be produced in accordance with the present invention include tissue factor and von Willebrands factor.

Enzymes

Another class of polypeptides that have been shown to be effective as pharmaceutical and/or commercial agents and that can desirably be produced according to the teachings of the present invention includes enzymes. Given the importance of recombinant enzymes in the treatment of diseases and other commercial and pharmaceutical uses, production of enzymes in accordance with the present invention is of particular interest. For example, the present invention may be used to produce enzymes in a cell culture wherein the misfolding and/or aggregation of the produced enzymes are reduced.

Enzymes may be glycoproteins whose glycosylation pattern affects enzymatic activity. Thus, the present invention may also be used to produce enzymes in a cell culture wherein the produced enzymes have a more extensive or otherwise more desirable glycosylation pattern.

As but one non-limiting example, a deficiency in glucocerebrosidase (GCR) results in a condition known as Gaucher's disease, which is caused by an accumulation of glucocerebrosidase in lysosomes of certain cells. Subjects with Gaucher's disease exhibit a range of symptoms including splenomegaly, hepatomegaly, skeletal disorder, thrombocytopenia and anemia. Friedman and Hayes showed that recombinant GCR (rGCR) containing a single substitution in the primary amino acid sequence exhibited an altered glycosylation pattern, specifically an increase in fucose and N-acetyl glucosamine residues compared to naturally occurring GCR (see U.S. Pat. No. 5,549,892, incorporated herein by reference in its entirety).

Friedman and Hayes also demonstrated that this rGCR exhibited improved pharmacokinetic properties compared to naturally occurring rGCR. For example, approximately twice as much rGCR targeted liver Kupffer cells than did naturally occurring GCR. Although the primary amino acid sequences of the two proteins differed at a single residue, Friedman and Hayes hypothesized that the altered glycosylation pattern of rGCR may also influence the targeting to Kupffer cells. One of ordinary skill in the art will be aware of other known examples of enzymes that exhibit altered enzymatic, pharmacokinetic and/or pharmacodynamic properties resulting from an alteration in their glycosylation patterns.

Growth Factors and Other Signaling Molecules

Another class of polypeptides that have been shown to be effective as pharmaceutical and/or commercial agents and that can desirably be produced according to the teachings of the present invention includes growth factors and other signaling molecules. Given the biological importance of growth factors and other signaling molecules and their importance as potential therapeutic agents, production of these molecules in accordance with the present invention is of particular interest. For example, the present invention may be used to produce growth factors or other signaling molecules in a cell culture wherein the misfolding and/or aggregation of the produced growth factors or other signaling molecules are reduced.

Growth factors are typically glycoproteins that are secreted by cells and bind to and activate receptors on other cells, initiating a metabolic or developmental change in the receptor cell. Thus, the present invention may also be used to produce growth factors or other signaling molecules in a cell culture wherein the produced growth factors or other signaling molecules have a more extensive or otherwise more desirable glycosylation pattern.

Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (TLs), e.g., IL-1 to IL-10; tumor necrosis factor (TNF) alpha and beta; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; prorelaxin; mouse gonadotropin-associated peptide; neurotrophic factors such as bone-derived neurotrophic factor (BDNF), neurotrophin-3, -4, -5, or -6 (NT-3, NT-4, NT-5, or NT-6), or a nerve growth factor such as NGF-beta. One of ordinary skill in the art will be aware of other growth factors or signaling molecules that can be expressed in accordance with methods and compositions of the present invention.

Specific alterations in the glycosylation pattern of growth factors or other signaling molecules have been shown to have dramatic effects on their therapeutic properties. As one example, a common method of treatment for patients who suffer from chronic anemia is to provide them with frequent injections of recombinant human erythropoietin (rHuEPO) in order to boost their production of red blood cells. An analog of rHuEPO, darbepoetin alfa (Aranesp®), has been developed to have a longer duration than normal rHuEPO. The primary difference between darbepoetin alfa and rHuEPO is the presence of two extra sialic-acid-containing N-linked oligosaccharide chains. Production of darbepoetin alfa has been accomplished using in vitro glycoengineering (see Elliott et al., Nature Biotechnology 21(4):414-21, 2003, incorporated herein by reference in its entirety). Elliott et al. used in vitro mutagenesis to incorporate extra glycosylation sites into the rHuEPO polypeptide backbone, resulting in expression of the darbepoetin alfa analog. The extra oligosaccharide chains are located distal to the EPO receptor binding site and apparently do not interfere with receptor binding. However, darbepoetin alfa's half-life is up to three-fold higher than rHuEPO, resulting in a much more effective therapeutic agent.

This example demonstrates that alterations in a growth factor or other signaling molecule's glycosylation pattern can have dramatic effects on the stability and/or activity of a therapeutic glycoprotein. Thus, expression of a growth factor or other signaling molecule of interest in accordance with methods and compositions of the present invention may result in the expressed growth factor or signaling molecule having an improved glycosylation pattern and improved therapeutic properties. In certain embodiments, a glycoprotein expressed in accordance with methods and compositions of the present invention will have either an increased or a more desirable sialylation pattern. In some embodiments, the sialylation pattern of a glycoprotein expressed in accordance with methods and compositions of the present invention will more accurately reflect the sialylation pattern of a natural or endogenous glycoprotein. In some embodiments, the sialylation pattern of a glycoprotein expressed in accordance with methods and compositions of the present invention will be different from the sialylation pattern of a natural or endogenous glycoprotein, resulting in a more desirable property or activity of that glycoprotein.

Receptors

Another class of polypeptides that have been shown to be effective as pharmaceutical and/or commercial agents and that can desirably be produced according to the teachings of the present invention includes receptors. Given the biological importance of receptors and their importance as potential therapeutic agents, production of these molecules in accordance with the present invention is of particular interest. For example, the present invention may be used to produce receptors in a cell culture wherein the misfolding and/or aggregation of the produced receptors are reduced.

Receptors are typically trans-membrane glycoproteins that function by recognizing an extra-cellular signaling ligand. Thus, the present invention may also be used to produce receptors in a cell culture wherein the produced receptors have a more extensive or otherwise more desirable glycosylation pattern. Receptors often have a protein kinase domain in addition to the ligand recognizing domain. This protein kinase domain initiates a signaling pathway by phosphorylating target intracellular molecules upon binding the ligand, leading to developmental or metabolic changes within the cell. In certain embodiments, an extracellular domain of a transmembrane receptor is produced in accordance with methods and systems disclosed herein. In certain embodiments, an intracellular domain of a transmembrane receptor is produced in accordance with methods and systems disclosed herein.

In certain embodiments, tumor necrosis factor inhibitors, in the form of tumor necrosis factor alpha and beta receptors (TNFR-1; EP 417,563 published Mar. 20, 1991; and TNFR-2, EP 417,014 published Mar. 20, 1991, each of which is incorporated herein by reference in its entirety) are expressed in accordance with systems and methods of the present invention (for review, see Naismith and Sprang, *J Inflamm.* 47(1-2): 1-7, 1995-96, incorporated herein by reference in its entirety). According to some embodiments, a tumor necrosis factor inhibitor comprises a soluble TNF receptor. In certain embodiments, a tumor necrosis factor inhibitor comprises a soluble TNFR-Ig. In certain embodiments, TNF inhibitors of the present invention are soluble forms of TNFRI and TNFRII. In certain embodiments, TNF inhibitors of the present invention are soluble TNF binding proteins. In certain embodiments, TNF inhibitors of the present invention are TNFR-Ig fusion proteins, e.g., TNFR-Fc or etanercept. As used herein, "etanercept," refers to TNFR-Fc, which is a dimer of two molecules of the extracellular portion of the p75 TNF-α receptor, each molecule consisting of a 235 amino acid Fc portion of human IgG1.

In some embodiments, receptors to be produced in accordance with the present invention are receptor tyrosine kinases (RTKs). The RTK family includes receptors that are crucial for a variety of functions numerous cell types (see, e.g., Yarden and Ullrich, *Ann. Rev. Biochem.* 57:433-478, 1988; Ullrich and Schlessinger, *Cell* 61:243-254, 1990, each of which is incorporated herein by reference). Non-limiting examples of RTKs include tumor necrosis factor alpha and beta receptors, members of the fibroblast growth factor (FGF) receptor family, members of the epidermal growth factor receptor (EGF) family, platelet derived growth factor (PDGF) receptor, tyrosine kinase with immunoglobulin and EGF homology domains-1 (TIE-1) and TIE-2 receptors (Sato et al., *Nature* 376(6535):70-74, 1995, incorporated herein by reference in its entirety) and c-Met receptor, some of which have been suggested to promote angiogenesis, directly or indirectly (Mustonen and Alitalo, *J. Cell Biol.* 129:895-898, 1995). Other non-limiting examples of RTK's include fetal liver kinase 1 (FLK-1) (sometimes referred to as kinase insert domain-containing receptor (KDR) (Terman et al., Oncogene 6:1677-83, 1991) or vascular endothelial cell growth factor receptor 2, VEGFR-2), fms-like tyrosine kinase-1 (Flt-1) (DeVries et al. Science 255; 989-991, 1992; Shibuya et al., Oncogene 5:519-524, 1990), sometimes referred to as vascular endothelial cell growth factor receptor 1 (VEGFR-1), neuropilin-1, endoglin, endosialin, and Axl. Those of ordinary skill in the art will be aware of other receptors that can be expressed in accordance with the present invention.

In certain embodiments, the receptor to be produced in accordance with the present invention is a G-protein coupled receptor (GPCR). GPCRs are a major target for drug action and development. In fact, receptors have led to more than half of the currently known drugs (Drews, *Nature Biotechnology,*

14:1516, 1996) and GPCRs represent the most important target for therapeutic intervention with 30% of clinically prescribed drugs either antagonizing or agonizing a GPCR (Milligan, G. and Rees, S., *TIPS*, 20:118-124, 1999). Since these receptors have an established, proven history as therapeutic targets, production of GPCRs in accordance with the present invention is also of particular interest.

GPCRs are proteins that have seven transmembrane domains. Upon binding of a ligand to a GPCR, a signal is transduced within the cell which results in a change in a biological or physiological property of the cell. GPCRs, along with G-proteins and effectors (intracellular enzymes and channels which are modulated by G-proteins), are the components of a modular signaling system that connects the state of intracellular second messengers to extracellular inputs. These genes and gene-products are potential causative agents of disease.

The GPCR protein superfamily now contains over 250 types of paralogues, receptors that represent variants generated by gene duplications (or other processes), as opposed to orthologues, the same receptor from different species. The superfamily can be broken down into five families: Family I, receptors typified by rhodopsin and the beta2-adrenergic receptor and currently represented by over 200 unique members; Family II, the recently characterized parathyroid hormone/calcitonin/secretin receptor family; Family III, the metabotropic glutamate receptor family in mammals; Family IV, the cAMP receptor family, important in the chemotaxis and development of D. discoideum; and Family V, the fungal mating pheromone receptors such as STE2.

GPCRs include receptors for biogenic amines, for lipid mediators of inflammation, peptide hormones, and sensory signal mediators. The GPCR becomes activated when the receptor binds its extracellular ligand. Conformational changes in the GPCR, which result from the ligand-receptor interaction, affect the binding affinity of a G protein to the GPCR intracellular domains. This enables GTP to bind with enhanced affinity to the G protein.

Activation of the G protein by GTP leads to the interaction of the G protein αsubunit with adenylate cyclase or other second messenger molecule generators. This interaction regulates the activity of adenylate cyclase and hence production of a second messenger molecule, cAMP. cAMP regulates phosphorylation and activation of other intracellular proteins. Alternatively, cellular levels of other second messenger molecules, such as cGMP or eicosinoids, may be upregulated or downregulated by the activity of GPCRs. The G protein a subunit is deactivated by hydrolysis of the GTP by GTPase, and the α, β, and γ subunits reassociate. The heterotrimeric G protein then dissociates from the adenylate cyclase or other second messenger molecule generator. Activity of GPCR may also be regulated by phosphorylation of the intra- and extracellular domains or loops.

Glutamate receptors form a group of GPCRs that are important in neurotransmission. Glutamate is the major neurotransmitter in the CNS and is believed to have important roles in neuronal plasticity, cognition, memory, learning and some neurological disorders such as epilepsy, stroke, and neurodegeneration (Watson, S. and S. Arkinstall, The G-Protein Linked Receptor Facts Book, Academic Press, San Diego Calif., pp. 130-132, 1994). The vasoactive intestinal polypeptide (VIP) family is a group of related polypeptides whose actions are also mediated by GPCRs. Key members of this family are VIP itself, secretin, and growth hormone releasing factor (GRF). VIP has a wide profile of physiological actions including relaxation of smooth muscles, stimulation or inhibition of secretion in various tissues, modulation of various immune cell activities, and various excitatory and inhibitory activities in the CNS. Secretin stimulates secretion of enzymes and ions in the pancreas and intestine and is also present in small amounts in the brain.

In general, practitioners of the present invention will select their protein or polypeptide of interest, and will know its precise amino acid sequence. Any given polypeptide that is to be expressed in accordance with the present invention will have its own particular characteristics and may influence the cell density or viability of the cultured cells, and may be expressed at lower levels than another polypeptide or protein grown under identical culture conditions. One of ordinary skill in the art will be able to appropriately modify inventive media and methods described herein in order to optimize cell growth, titer, glycosylation, folding or any other property of a given expressed polypeptide or protein.

Introduction of Genes for the Expression of Polypeptide into Host Cells

In certain embodiments, a nucleic acid molecule introduced into the cell encodes the polypeptide desired to be expressed according to the present invention. In certain embodiments, a nucleic acid molecule may encode a gene product that induces the expression of the desired polypeptide by the cell. For example, the introduced genetic material may encode a transcription factor that activates transcription of an endogenous or heterologous polypeptide. Alternatively or additionally, the introduced nucleic acid molecule may increase the translation or stability of a polypeptide expressed by the cell.

Methods suitable for introducing nucleic acids sufficient to achieve expression of a polypeptide of interest into mammalian host cells are known in the art. See, for example, Gething et al., *Nature*, 293:620-625, 1981; Mantei et al., *Nature*, 281: 40-46, 1979; Levinson et al. EP 117,060; and EP 117,058, each of which is incorporated herein by reference. For mammalian cells, common methods of introducing genetic material into the cell include the calcium phosphate precipitation method of Graham and van der Erb, Virology, 52:456-457, 1978 or the Lipofectamine™ (Gibco BRL) Method of Hawley-Nelson, Focus 15:73, 1993. General aspects of mammalian cell host system transformations have been described by Axel in U.S. Pat. No. 4,399,216 issued Aug. 16, 1983. For various techniques for introducing genetic material into mammalian cells, see Keown et al., *Methods in Enzymology*, 185:527-537, 1990, and Mansour et al., *Nature*, 336:348-352, 1988.

In certain embodiments, the nucleic acid to be introduced is in the form of a naked nucleic acid molecule. In some aspects of these embodiments, the nucleic acid molecule introduced into a cell consists only of the nucleic acid encoding the polypeptide and the necessary genetic control elements. In some aspects of these embodiments, the nucleic acid encoding the polypeptide (including the necessary regulatory elements) is contained within a plasmid vector. Non-limiting representative examples of suitable vectors for expression of polypeptide in mammalian cells include pCDNA1; pCD, see Okayama, et al., *Mol. Cell Biol.* 5:1136-1142, 1985; pMClneo Poly-A, see Thomas, et al., *Cell* 51:503-512, 1987; a baculovirus vector such as pAC 373 or pAC 610; CDM8 (Seed, B., *Nature* 329:840, 1987) and pMT2PC (Kaufman, et al., EMBO J. 6:187-195, 1987). In certain embodiments, the nucleic acid molecule to be introduced into a cell is contained within a viral vector. For example, the nucleic acid encoding the polypeptide may be inserted into the viral genome (or a partial viral genome). The regulatory elements directing the expression of the polypeptide can be included with the nucleic acid inserted into the viral genome (i.e., linked to the gene inserted into the viral genome) or can be provided by the viral genome itself.

Naked DNA can be introduced into cells by forming a precipitate containing the DNA and calcium phosphate. Additionally or alternatively, naked DNA can also be introduced into cells by forming a mixture of the DNA and DEAE-dextran and incubating the mixture with the cells or by incubating the cells and the DNA together in an appropriate buffer and subjecting the cells to a high-voltage electric pulse (i.e., by electroporation). In some embodiments, naked DNA is introduced into cells by mixing the DNA with a liposome suspension containing cationic lipids. The DNA/liposome complex is then incubated with cells. Naked DNA can also be directly injected into cells by, for example, microinjection.

Additionally or alternatively, naked DNA can be introduced into cells by complexing the DNA to a cation, such as polylysine, which is coupled to a ligand for a cell-surface receptor (see for example Wu, G. and Wu, C. H., *J. Biol. Chem.* 263:14621, 1988; Wilson et al., *J. Biol. Chem.* 267: 963-967, 1992; and U.S. Pat. No. 5,166,320). Binding of the DNA-ligand complex to the receptor facilitates uptake of the DNA by receptor-mediated endocytosis.

Use of viral vectors containing particular nucleic acid sequences, e.g., a cDNA encoding a polypeptide, is a common approach for introducing nucleic acid sequences into a cell. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are generally expressed efficiently in cells that have taken up viral vector nucleic acid.

Defective retroviruses are well characterized for use in gene transfer for gene therapy purposes (for a review see Miller, A. D., *Blood* 76:271, 1990). A recombinant retrovirus can be constructed having a nucleic acid encoding a polypeptide of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques.

The genome of an adenovirus can be manipulated such that it encodes and expresses a polypeptide of interest but is inactivated in terms of its ability to replicate in a normal lytic viral life cycle. See, for example, Berkner et al., *BioTechniques* 6:616, 1988; Rosenfeld et al., *Science* 252:431-434, 1991; and Rosenfeld et al., *Cell* 68:143-155, 1992. Suitable adenoviral vectors derived from the adenovirus strain Ad type 5 dl324 or other strains of adenovirus (e.g., Ad2, Ad3, Ad7 etc.) are known in the art. Recombinant adenoviruses are advantageous in that they do not require dividing cells to be effective gene delivery vehicles and can be used to infect a wide variety of cell types, including airway epithelium (Rosenfeld et al., 1992, cited supra), endothelial cells (Lemarchand et al., *Proc. Natl. Acad. Sci. USA* 89:6482-6486, 1992), hepatocytes (Herz and Gerard, *Proc. Natl. Acad. Sci. USA* 90:2812-2816, 1993) and muscle cells (Quantin et al., *Proc. Natl. Acad. Sci. USA* 89:2581-2584, 1992). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., cited supra; Haj-Ahmand and Graham, *J. Virol.* 57:267, 1986). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al., *Curr. Topics in Micro. and Immunol.* 158:97-129, 1992). It is also one of the few viruses that may integrate its DNA into non-dividing cells, and exhibits a high frequency of stable integration (see for example Flotte et al., *Am. J. Respir. Cell Mol. Biol.* 7:349-356, 1992; Samulski et al., *J. Virol.* 63:3822-3828, 1989; and McLaughlin et al., *J. Virol.* 62:1963-1973, 1989). Vectors containing as little as 300 base pairs of AAV can be packaged and can integrate. Space for exogenous DNA is limited to about 4.5 kb. An AAV vector such as that described in Tratschin et al., (*Mol. Cell. Biol.* 5:3251-3260, 1985) can be used to introduce DNA into cells. A variety of nucleic acids have been introduced into different cell types using AAV vectors (see for example Hermonat et al., *Proc. Natl. Acad. Sci. USA* 81:6466-6470, 1984; Tratschin et al., *Mol. Cell. Biol.* 4:2072-2081, 1985; Wondisford et al., *Mol. Endocrinol.* 2:32-39, 1988; Tratschin et al, *J. Virol.* 51:611-619, 1984; and Flotte et al., *J. Biol. Chem.* 268:3781-3790, 1993).

When the method used to introduce nucleic acid molecules into a population of cells results in modification of a large proportion of the cells and efficient expression of the polypeptide by the cells, the modified population of cells may be used without further isolation or subcloning of individual cells within the population. That is, there may be sufficient production of the polypeptide by the population of cells such that no further cell isolation is needed and the population can be immediately be used to seed a cell culture for the production of the polypeptide. In some embodiments, it may be desirable to isolate and expand a homogenous population of cells from a single cell that efficiently produces the polypeptide.

Alternative to introducing a nucleic acid molecule into a cell that encodes a polypeptide of interest, an introduced nucleic acid may encode another polypeptide, protein or regulatory element that induces or increases the level of expression of the protein or polypeptide produced endogenously by a cell. For example, a cell may be capable of expressing a particular polypeptide but may fail to do so without additional treatment of the cell. Similarly, the cell may express insufficient amounts of the polypeptide for the desired purpose. Thus, an agent that stimulates expression of the polypeptide of interest can be used to induce or increase expression of that polypeptide by the cell. For example, an introduced nucleic acid molecule may encode a transcription factor that activates or upregulates transcription of the polypeptide of interest. Expression of such a transcription factor in turn leads to expression, or more robust expression, of the polypeptide of interest. Similarly, the introduced nucleic acid molecule may contain one or more regulatory elements that titrate away one or more transcriptional repressors from a regulatory region of the polypeptide of interest.

In certain embodiments, a nucleic acid that directs expression of the polypeptide is stably introduced into the host cell. In certain embodiments, a nucleic acid that directs expression of the polypeptide is transiently introduced into the host cell. One of ordinary skill in the art will be able to choose whether to stably or transiently introduce the nucleic acid into the cell based on his or her experimental needs.

A gene encoding the polypeptide of interest may optionally be linked to one or more regulatory genetic control elements. In some embodiments, a genetic control element directs constitutive expression of the polypeptide. In some embodiments, a genetic control element that provides inducible expression of a gene encoding the polypeptide of interest can be used. Use of an inducible genetic control element (e.g., an inducible promoter) allows for modulation of the production of the polypeptide in the cell. Non-limiting examples of potentially useful inducible genetic control elements for use in eukaryotic cells include hormone-regulated elements (see e.g., Mader, S. and White, J. H., *Proc. Natl. Acad. Sci. USA* 90:5603-5607, 1993), synthetic ligand-regulated elements (see, e.g. Spencer, D. M. et al., *Science* 262:1019-1024, 1993) and ionizing radiation-regulated elements (see e.g., Manome, Y. et al., *Biochemistry* 32:10607-10613, 1993; Datta, R. et al., *Proc. Natl. Acad. Sci. USA* 89:10149-10153, 1992). Additional cell-specific or other regulatory systems known in the art may be used in accordance with methods and compositions described herein.

One of ordinary skill in the art will be able to choose and, optionally, to appropriately modify the method of introducing genes that cause the cell to express the polypeptide of interest in accordance with the teachings of the present invention.

Isolation of Expressed Polypeptide

In certain embodiments, it is desirable to isolate and/or purify proteins or polypeptides expressed according to the present invention. In certain embodiments, an expressed polypeptide or protein is secreted into the medium and thus cells and other solids may be removed, as by centrifugation or filtering for example, as a first step in the purification process.

In some embodiments, an expressed polypeptide or protein is bound to the surface of the host cell. In such embodiments, the media is removed and the host cells expressing the polypeptide or protein are lysed as a first step in the purification process. Lysis of mammalian host cells can be achieved by any number of means known to those of ordinary skill in the art, including physical disruption by glass beads and exposure to high pH conditions.

A polypeptide or protein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, *Protein Purification Principles and Practice 2nd Edition*, Springer-Verlag, N.Y., 1987; Higgins, S. J. and Hames, B. D. (eds.), *Protein Expression: A Practical Approach*, Oxford Univ Press, 1999; and Deutscher, M. P., Simon, M. I., Abelson, J. N. (eds.), *Guide to Protein Purification: Methods in Enzymology* (Methods in Enzymology Series, Vol 182), Academic Press, 1997, each of which is incorporated herein by reference in its entirety). For immunoaffinity chromatography in particular, the protein may be isolated by binding it to an affinity column comprising antibodies that were raised against that protein and were affixed to a stationary support. Affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly advantageous when cells must be lysed in order to isolate and purify the expressed polypeptide or protein.

Proteins or polypeptides expressed according to certain methods of the present invention may have more extensive and/or modified glycosylation patterns than they would if grown under non-inventive cell culture conditions. Thus, one practical benefit of the present invention that may be exploited at the purification step is that the additional and/or modified sugar residues present on a glycoprotein grown in accordance with certain of the present inventive methods and/or compositions may confer on it distinct biochemical properties that may be used by the practitioner to purify that glycoprotein more easily, or to a greater purity, than would be possible for a glycoprotein grown in accordance with non-inventive methods and/or compositions.

One of ordinary skill in the art will appreciate that the exact purification technique may vary depending on the character of the polypeptide or protein to be purified, the character of the cells from which the polypeptide or protein is expressed, and/or the composition of the medium in which the cells were grown.

Immunogenic Compositions

Proteins or polypeptides produced according to the teachings of the present disclosure may also be used in immunogenic compositions, e.g., as vaccines. In certain embodiments, a reduction in the misfolding and/or aggregation of the produced protein or polypeptide results in a more effective immunogenic composition.

In certain embodiments, an improved glycosylation pattern achieved by producing glycoproteins in accordance with certain methods and/or compositions of the present invention results in a more effective immunogenic composition. For example, an immunogenic composition containing the produced glycoprotein may trigger a more effective immune response in which the subject's immune system produces a greater number of antibodies to the glycoprotein and/or produces antibodies that exhibit a greater specificity for a the immunogenic glycoprotein. Additionally or alternatively, the glycoprotein may trigger an immune response with fewer and/or less severe side effects. In certain embodiments, inventive immunogenic compositions comprise one or more glycoproteins. Additionally or alternatively, an inventive immunogenic composition may include one or more physiologically acceptable carriers.

In general, selection of the appropriate "effective amount" or dosage for components of an inventive immunogenic composition(s) is typically based upon a variety of factors, including but not limited to, the identity of the selected polypeptide(s) in the immunogenic composition employed, the glycosylation pattern of the polypeptide(s), and the physical condition of the subject, most especially including the general health, age and weight of the immunized subject. As is known in the art, the particular methods and routes of administration and the presence of additional components in the immunogenic compositions may also affect the dosages and amounts of the DNA plasmid compositions. Such selection and upward or downward adjustment of the effective dose is within the skill of the art. The amount of immunogenic composition required to induce an immune response, including but not limited to a protective response, or produce an exogenous effect in the patient without significant adverse side effects varies depending upon these factors. Suitable doses are readily determined by persons skilled in the art.

Certain immunogenic compositions of the present invention may contain an adjuvant. An adjuvant is a substance that enhances the immune response when administered together with an immunogen or antigen. A number of cytokines or lymphokines have been shown to have immune modulating activity, and thus may be used as adjuvants, including, but not limited to, the interleukins 1-α, 1-β, 2, 4, 5, 6, 7, 8, 10, 12 (see, e.g., U.S. Pat. No. 5,723,127, incorporated herein by reference in its entirety), 13, 14, 15, 16, 17 and 18 (and its mutant forms), the interferons-α, β and γ, granulocyte-macrophage colony stimulating factor (see, e.g., U.S. Pat. No. 5,078,996, incorporated herein by reference in its entirety), macrophage colony stimulating factor, granulocyte colony stimulating factor, GSF, and the tumor necrosis factors α and β. Still other adjuvants useful in this invention include a chemokine, including without limitation, MCP-1, MIP-1α, MIP-1β, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Still another adjuvant molecule includes Caspase (ICE). See, also International Patent Publication Nos. WO98/17799 and WO99/43839, each of which is incorporated herein by reference in its entirety.

Also useful as adjuvants are cholera toxins (CT) and mutants thereof, including those described in published International Patent Application number WO 00/18434 (wherein the glutamic acid at amino acid position 29 is replaced by another amino acid (other than aspartic acid, for example a histidine). Similar CTs or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36). Each of these references is incorporated herein in its entirety.

In certain embodiments, immunogenic compositions of the present invention are administered to a human or to a non-human vertebrate by a variety of routes including, but not limited to, intranasal, oral, vaginal, rectal, parenteral, intradermal, transdermal (see for example, International patent publication No. WO 98/20734, which is hereby incorporated by reference in its entirety), intramuscular, intraperitoneal, subcutaneous, intravenous and intraarterial. The appropriate route may be selected depending on the nature of the immunogenic composition used, an evaluation of the age, weight, sex and general health of the patient and the antigens present in the immunogenic composition, and/or other factors known to those of ordinary skill in the art.

In certain embodiments, immunogenic compositions are administered at multiple times. The order of immunogenic composition administration and the time periods between individual administrations may be selected by one of skill in the art based upon relevant factors known to those of ordinary skill in the art, including but not limited to the physical characteristics and precise responses of the host to the application of the method.

Pharmaceutical Formulations

In certain embodiments, produced polypeptides or proteins will have pharmacologic activity and will be useful in the preparation of pharmaceuticals. Inventive compositions as described above may be administered to a subject or may first be formulated for delivery by any available route including, but not limited to parenteral, intravenous, intramuscular, intradermal, subcutaneous, oral, buccal, sublingual, nasal, bronchial, opthalmic, transdermal (topical), transmucosal, rectal, and vaginal routes. Inventive pharmaceutical compositions typically include a purified polypeptide or protein expressed from a mammalian cell line, a delivery agent (i.e., a cationic polymer, peptide molecular transporter, surfactant, etc., as described above) in combination with a pharmaceutically acceptable carrier. As used herein, the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into compositions of the present invention. For example, a protein or polypeptide produced according to the present invention may be conjugated to drugs for systemic pharmacotherapy, such as toxins, low-molecular-weight cytotoxic drugs, biological response modifiers, and radionuclides (see e.g., Kunz et al., Calicheamicin derivative-carrier conjugates, US20040082764 A1). Additional ingredients useful in preparing pharmaceutical compositions in accordance with the present invention include, for example, flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof.

Alternatively or additionally, a protein or polypeptide produced according to the present invention may be administered in combination with (whether simultaneously or sequentially) one or more additional pharmaceutically active agents. An exemplary list of these pharmaceutically active agents can be found in the Physicians' Desk Reference, 55 Edition, published by Medical Economics Co., Inc., Montvale, N.J., 2001, incorporated herein by reference in its entirety. For many of these listed agents, pharmaceutically effective dosages and regimens are known in the art; many are presented in the Physicians' Desk Reference itself.

Solid pharmaceutical compositions may contain one or more solid carriers, and optionally one or more other additives such as flavoring agents, lubricants, solubilizers, suspending agents, fillers, glidants, compression aids, binders or tablet-disintegrating agents or an encapsulating material. suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier may be a finely divided solid which is in admixture with the finely divided active ingredient. In tablets, the active ingredient is generally mixed with a carrier having the necessary compression properties in suitable proportions, and optionally, other additives, and compacted into the desired shape and size.

Liquid pharmaceutical compositions may contain the polypeptide or protein expressed according to the present invention and one or more liquid carriers to form solutions, suspensions, emulsions, syrups, elixirs, or pressurized compositions. Pharmaceutically acceptable liquid carriers include, for example water, organic solvents, pharmaceutically acceptable oils or fat, or combinations thereof. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators, or combinations thereof. If the liquid formulation is intended for pediatric use, it is generally desirable to avoid inclusion of, or limit the amount of, alcohol.

Examples of liquid carriers suitable for oral or parenteral administration include water (optionally containing additives such as cellulose derivatives such as sodium carboxymethyl cellulose), alcohols or their derivatives (including monohydric alcohols or polyhydric alcohols such as glycols) or oils (e.g., fractionated coconut oil and arachis oil). For parenteral administration the carrier can also be an oily ester such as ethyl oleate and isopropyl myristate. The liquid carrier for pressurized compositions can be halogenated hydrocarbons or other pharmaceutically acceptable propellant.

Liquid pharmaceutical compositions which are sterile solutions or suspensions can be administered parenterally, for example by, intramuscular, intraperitoneal, epidural, intrathecal, intravenous or subcutaneous injection. Pharmaceutical compositions for oral or transmucosal administration may be either in liquid or solid composition form.

In certain embodiments, a pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Advantageously, certain pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In certain cases, it will be useful to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the purified polypeptide or protein in the required amount in an appropriate solvent with one or a combination of ingredients enumerated above, as required, followed by filtered sterilization. Generally, dispersions are prepared by incorporating the purified polypeptide or protein expressed from a mammalian cell line into a sterile vehicle which contains a basic dispersion medium and the required other ingredients from those enumerated above. In the case of sterile powders for the preparation of sterile injectable solutions, advantageous methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the purified polypeptide or protein can be incorporated with excipients and used in the form of tablets, troches, or capsules, e.g., gelatin capsules. Oral compositions can also be prepared using a fluid carrier, e.g., for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Such preparations may be mixed chewable or liquid formulations or food materials or liquids if desirable, for example to facilitate administration to children, to individuals whose ability to swallow tablets is compromised, or to animals. Formulations for oral delivery may advantageously incorporate agents to improve stability within the gastrointestinal tract and/or to enhance absorption.

For administration by inhalation, inventive compositions comprising a purified polypeptide or protein expressed from a mammalian cell line and a delivery agent can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered, for example a therapeutically effective amount. The present invention particularly contemplates delivery of inventive compositions using a nasal spray, inhaler, or other direct delivery to the upper and/or lower airway. Intranasal administration of DNA vaccines directed against influenza viruses has been shown to induce CD8 T cell responses, indicating that at least some cells in the respiratory tract can take up DNA when delivered by this route, and inventive delivery agents will enhance cellular uptake. According to certain embodiments, compositions comprising a purified polypeptide expressed from a mammalian cell line and a delivery agent are formulated as large porous particles for aerosol administration.

Modified release and pulsatile release oral dosage forms may contain excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release oral dosage forms may contain one or a combination of release rate modifying excipients. Release rate modifying excipients may be present both within the dosage form i.e., within the matrix, and/or on the dosage form, i.e., upon the surface or coating.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified polypeptide or protein and delivery agents can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Alternatively, the compounds can be administered in the form of a suppository or pessary, or they may be applied topically in the form of a gel, hydrogel, lotion or other glycerides, solution, cream, ointment or dusting powder.

In some embodiments, compositions are prepared with carriers that will protect the polypeptide or protein against rapid elimination from the body, such as a controlled release formulation, including implants and microencapsulated delivery systems. In general, inventive compositions may be formulated for immediate, delayed, modified, sustained, pulsed, or controlled-release delivery. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Suitable materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Proteins and polypeptides produced according to the present invention may also be used in combination with a cyclodextrin. Cyclodextrins are known to form inclusion and non-inclusion complexes with certain molecules. Formation of a cyclodextrin complex may modify the solubility, dissolution rate, bioavailability and/or stability property of a protein or polypeptide. Cyclodextrin complexes are generally useful for most dosage forms and administration routes. As an alternative to direct complexation with the protein or polypeptide, the cyclodextrin may be used as an auxiliary additive, e.g. as a carrier, diluent or solubiliser. Alpha-, beta- and gamma-cyclodextrins are most commonly used and suitable examples are described in published international patent applications WO91/11172, WO94/02518 and WO98/55148.

In some embodiments, pharmaceutical compositions of the present invention are provided in unit dosage form, such as tablets or capsules. It may be advantageous to formulate oral or parenteral compositions in unit dosage form for ease of administration and uniformity of dosage. In such form, the composition is sub-divided in unit dose containing appropriate quantities of the polypeptide or protein. The unit dosage forms can be packaged compositions, for example packeted powders, vials, ampoules, pre-filled syringes or sachets containing liquids. The unit dosage form can be, for example, a capsule or tablet itself, or it can be an appropriate number of any such compositions in package form. As one skilled in the art will recognize, therapeutically effective unit dosage will depend on several factors, including, for example, the method of administration, the potency of the polypeptide or protein, and/or the weight of the recipient and the identities of other components in the pharmaceutical composition.

A polypeptide or protein expressed according to the present invention can be administered at various intervals and over different periods of time as required, e.g., one time per week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a polypeptide or protein as described herein may comprise a single treatment or a series of treatments. It is furthermore understood that appropriate doses may depend upon the potency of the polypeptide or protein and may optionally be tailored to the particular recipient, for example, through administration of increasing doses until a preselected desired response is achieved. It is understood that the specific dose level for any particular animal subject may depend upon a variety of factors including the activity of the specific polypeptide or protein employed, the age, body weight, general health, gender, and diet of the subject, the time of administration, the route of administration, the rate of excretion, any drug combination, and the degree of expression or activity to be modulated.

The present invention encompasses the use of inventive compositions for treatment of nonhuman animals. Accordingly, doses and methods of administration may be selected in accordance with known principles of veterinary pharmacology and medicine. Guidance may be found, for example, in Adams, R. (ed.), *Veterinary Pharmacology and Therapeutics*, 8$^{th}$ edition, Iowa State University Press; ISBN: 0813817439; 2001.

Inventive pharmaceutical compositions can be included in a container, pack, or dispenser together with instructions for administration.

EXAMPLES

Example 1

Medium Formulations

The present invention encompasses the finding that polypeptides produced by a culture of cells grown in culture media containing copper and/or glutamate at one or more inventive concentrations exhibit reduced levels of misfolding and/or aggregation than they otherwise would if the cells were grown in traditional media. The present invention also encompasses the finding that polypeptides produced by a culture of cells grown in culture media containing copper and/or glutamate at one or more inventive concentrations exhibit an increase in total glycosylation than would otherwise be observed if the cells were grown in traditional media. Copper and/or glutamate may be added to any culture medium that is capable of supporting cell growth. Exemplary culture media to which copper and/or glutamate may be added to within any of the inventive concentrations are listed in Table 1, although the present invention is not limited to the utilization of these culture media. As will be understood by one of ordinary skill in the art, other culture media may be utilized to grow cells and/or certain alterations may be made to the compositions of the exemplary culture media listed in Table 1.

TABLE 1

Exemplary culture media.

| | Medium A | | Medium B | | Medium C | | Medium D | | Medium E | |
|---|---|---|---|---|---|---|---|---|---|---|
| Amino Acids | mg/L | mM | mg/L | mM | mg/L | mM | mg/L | mM | mg/L | mM |
| alanine | 96.03 | 1.08 | 24.87 | 0.28 | 17.80 | 0.20 | | | 24.87 | 0.28 |
| arginine | 1186.99 | 6.82 | 423.43 | 2.43 | 696.00 | 4.00 | 84.00 | 0.40 | 423.43 | 2.43 |
| asparagine•$H_2O$ | 713.59 | 4.76 | 173.90 | 1.16 | 3000 | 20.00 | | | 173.90 | 1.16 |
| aspartic acid | 318.53 | 2.39 | 52.72 | 0.40 | 219.45 | 1.65 | | | 52.72 | 0.40 |
| cysteine•HCl•$H_2O$ | 70.01 | 0.40 | 70.01 | 0.40 | 70.40 | 0.40 | 35.10 | 0.20 | 70.01 | 0.40 |
| cysteine•2HCl | 297.09 | 0.95 | 62.09 | 0.20 | 468.75 | 1.50 | | | 62.09 | 0.20 |
| glutamic acid | | | | | | | | | 41.08 | 0.28 |
| monosodium glutamate | 158.59 | 1.08 | 41.08 | 0.28 | 33.80 | 0.20 | | | | |
| glutamine | 1892.40 | 12.96 | 1162.40 | 7.96 | 584.00 | 4.00 | 584.60 | 4.00 | 1162 | 7.96 |
| glycine | 95.88 | 1.28 | 35.92 | 0.48 | 115.50 | 1.54 | 30.00 | 0.40 | 35.92 | 0.48 |
| histidine•HCl•$H_2O$ | 369.10 | 1.76 | 75.27 | 0.36 | 474.60 | 2.26 | 42.00 | 0.20 | 75.27 | 0.36 |
| isoleucine | 623.63 | 4.76 | 151.90 | 1.16 | 570.73 | 4.36 | 104.80 | 0.80 | 151.90 | 1.16 |
| leucine | 852.31 | 6.51 | 172.69 | 1.32 | 1030 | 7.87 | 104.80 | 0.80 | 172.69 | 1.32 |
| lysine•HCl | 945.96 | 5.20 | 218.38 | 1.20 | 1401 | 7.70 | 146.20 | 0.80 | 218.38 | 1.20 |
| methionine | 291.82 | 1.96 | 53.55 | 0.36 | 387.40 | 2.60 | 30.00 | 0.20 | 53.55 | 0.36 |
| phenylalanine | 428.62 | 2.60 | 98.81 | 0.60 | 507.00 | 3.07 | 66.00 | 0.40 | 98.81 | 0.60 |
| proline | 372.25 | 3.24 | 96.40 | 0.84 | 539.50 | 4.69 | | | 96.40 | 0.84 |
| serine | 904.71 | 8.62 | 273.07 | 2.60 | 1052 | 10.02 | | | 273.07 | 2.60 |
| threonine | 513.39 | 4.31 | 132.81 | 1.12 | 564.80 | 4.75 | 95.20 | 0.80 | 132.81 | 1.12 |
| tryptophan | 159.32 | 0.78 | 28.99 | 0.14 | 274.16 | 1.34 | 16.00 | 0.08 | 28.99 | 0.14 |
| tyrosine•2Na•$2H_2O$ | 560.81 | 2.15 | 145.10 | 0.56 | 745.75 | 2.86 | 89.46 | 0.40 | 145.10 | 0.56 |
| valine | 505.36 | 4.32 | 131.17 | 1.12 | 749.00 | 6.40 | 93.60 | 0.80 | 131.17 | 1.12 |
| Vitamins | mg/L | μM | mg/L | μM | mg/L | μM | mg/L | μM | mg/L | μM |
| biotin | 2.00 | 8.21 | 0.36 | 1.49 | 2.68 | 11.00 | | | 0.36 | 1.49 |
| calcium pantothenate | 22.02 | 46.27 | 4.03 | 8.47 | 21.92 | 46.06 | 4.00 | 8.40 | 4.03 | 8.47 |
| choline chloride | 87.67 | 630.74 | 16.11 | 115.92 | 158.46 | 1140. | 4.00 | 28.60 | 16.11 | 115.92 |
| folic acid | 25.95 | 58.84 | 4.76 | 10.80 | 25.93 | 58.80 | 4.00 | 9.10 | 4.76 | 10.80 |
| inositol | 123.39 | 685.47 | 22.64 | 125.79 | 163.98 | 911.00 | 7.00 | 38.90 | 22.64 | 125.79 |
| nicotinamide | 19.60 | 160.70 | 3.61 | 29.62 | 26.23 | 215.00 | 4.00 | 32.80 | 3.61 | 29.62 |
| pyridoxal•HCl | 1.99 | 9.83 | 1.99 | 9.83 | 2.03 | 10.00 | 4.00 | 19.60 | 1.99 | 9.83 |
| pyridoxine•HCl | 18.06 | 87.67 | 1.67 | 8.10 | 36.13 | 175.38 | | | 1.67 | 8.10 |
| riboflavin | 2.20 | 5.85 | 0.40 | 1.06 | 2.41 | 6.42 | 0.40 | 1.10 | 0.40 | 1.06 |
| thiamine•HCl | 21.51 | 63.84 | 3.92 | 11.64 | 39.43 | 117.00 | 4.00 | 11.90 | 3.92 | 11.64 |
| vitamin B12 | 6.93 | 5.12 | 1.34 | 0.99 | 21.17 | 15.62 | | | 1.34 | 0.99 |
| Inorganic Salts | μg/L | mM | μg/L | mM | μg/L | mM | μg/L | mM | μg/L | mM |
| $CaCl_2$ | 115.78 | 1.04 | 115.78 | 1.04 | 116.55 | 1.05 | 200.0 | 1.80 | 115.78 | 1.04 |
| KCl | 310.94 | 4.17 | 310.94 | 4.17 | 312.90 | 4.19 | 400.0 | 5.40 | 310.94 | 4.17 |
| $Na_2HPO_4$ | 70.81 | 0.50 | 70.81 | 0.50 | 56.60 | 0.40 | | | 70.81 | 0.50 |
| NaCl | 1104.96 | 18.92 | 3704.96 | 63.44 | 1100 | 18.80 | 6400.0 | 110.30 | 3704 | 63.44 |
| $NaH_2PO_4$•$H_2O$ | 636.33 | 4.61 | 114.53 | 0.83 | 645.84 | 4.68 | 140.0 | 0.91 | 114.33 | 0.83 |
| $MgSO_4$ | 48.70 | 0.41 | 48.70 | 0.41 | | | | | 48.70 | 0.41 |
| $MgSO_4$•$7H_2O$ | 95.00 | 0.39 | 8.60 | 0.03 | 138.00 | 1.15 | 200.0 | 0.80 | 8.60 | 0.03 |
| $MgCl_2$ | 28.53 | 0.30 | 28.53 | 0.30 | 28.50 | 0.30 | | | 28.53 | 0.30 |
| $NaHCO_3$ | 2000.00 | 23.81 | 1220.00 | 14.52 | 2000 | 23.81 | 3700.0 | 44.00 | 2440 | 29.04 |
| Trace Elements | μg/L | nM | μg/L | nM | μg/L | nM | μg/L | nM | μg/L | nM |
| Sodium Selenite | 28.00 | 161.94 | 7.00 | 40.49 | 69.16 | 400.00 | | | 7.00 | 40.49 |
| $Fe(NO_3)_3$•$9H_2O$ | 49.86 | 123.42 | 49.86 | 123.42 | 50.00 | 123.76 | 0.10 | 250 | 49.86 | 123.42 |
| $CuSO_4$ | 2.69 | 16.80 | 0.97 | 6.06 | 10.24 | 64.00 | | | 0.97 | 6.06 |
| $CuSO_4$•$5H_2O$ | 11.24 | 45.00 | 7.49 | 30.00 | 99.88 | 400.00 | | | 7.49 | 30.00 |
| $FeSO_4$•$7H_2O$ | 2503.85 | 9006.64 | 1542 | 5549 | 4170 | 15000 | | | 1542 | 5549 |
| $ZnSO_4$•$7H_2O$ | 2734.77 | 9528.82 | 1383 | 4821 | 2640 | 9200 | | | 1383 | 4821 |
| $MnSO_4$•$H_2O$ | 0.26 | 1.51 | 0.17 | 1.01 | 33.80 | 200.00 | | | 0.17 | 1.01 |
| $Na2SiO3$•$9H_2O$ | 210.00 | 739.27 | 140 | 492.84 | 284.07 | 1000 | | | 140.00 | 492.84 |
| $(NH4)_6Mo_7O_{24}$•$4H_2O$ | 1.86 | 1.50 | 1.24 | 1.00 | 247.20 | 200.00 | | | 1.24 | 1.00 |
| $NH_4VO_3$ | 0.98 | 8.33 | 0.65 | 5.56 | 2.34 | 20.00 | | | 0.65 | 5.56 |
| $NiSO_4$•$6H_2O$ | 0.20 | 0.74 | 0.13 | 0.49 | 5.26 | 20.00 | | | 0.13 | 0.49 |

TABLE 1-continued

Exemplary culture media.

| Amino Acids | Medium A mg/L | Medium A mM | Medium B mg/L | Medium B mM | Medium C mg/L | Medium C mM | Medium D mg/L | Medium D mM | Medium E mg/L | Medium E mM |
|---|---|---|---|---|---|---|---|---|---|---|
| SnCl$_2$•2H$_2$O | 0.18 | 0.80 | 0.12 | 0.53 | 0.90 | 4.00 | | | 0.12 | 0.53 |
| AlCl$_3$•6H$_2$O | | | | | 0.97 | 4.00 | | | | |
| KBr | | | | | 0.48 | 4.00 | | | | |
| CrCl$_3$ | | | | | 15.83 | 100.00 | | | | |
| NaF | | | | | 0.17 | 4.00 | | | | |
| GeO$_2$ | | | | | 0.42 | 4.00 | | | | |
| KI | | | | | 33.20 | 200.00 | | | | |
| RbCl | | | | | 0.48 | 4.00 | | | | |
| H$_3$BO$_3$ | | | | | 12.37 | 200.00 | | | | |
| LiCl | | | | | 0.17 | 4.00 | | | | |

| Other Components | mg/L | μM | mg/L | μM | mg/L | μM | mg/L | μM | mg/L | μM |
|---|---|---|---|---|---|---|---|---|---|---|
| Hydrocortisone | 0.23 | 0.64 | .0864 | .24 | 540.00 | 1.49 | | | 0.09 | 0.24 |
| Putrescine•2HCl | 6.48 | 40.22 | 2.48 | 15.39 | 15000 | 93.11 | | | 2.48 | 15.39 |
| linoleic acid | 0.22 | 0.80 | 0.057 | 0.20 | 290.00 | 1.04 | | | 0.06 | 0.20 |
| thioctic acid | 0.56 | 2.73 | 0.14 | 0.69 | 716.00 | 3.48 | | | 0.14 | 0.69 |
| D-glucose (Dextrose) | 16039 | 89107 | 11042 | 61350 | 15000 | 83.33 | 4500 | 25000 | 11042 | 61345 |
| PVA | 2560 | | 2520 | | 2560 | | 2400 | | 2520 | 0.00 |
| Nucellin | 54.00 | | 14.00 | | 50.00 | | 10.00 | | 14.00 | 0.00 |
| Sodium Pyruvate | 54.85 | 498.63 | 54.85 | 500 | 55.00 | 0.50 | 110.0 | 1000 | 54.85 | 498.63 |

In certain embodiments, cells are supplemented at one or more times after the initial culture is begun with one or more feed media. Exemplary feed media are listed in Table 2, although the present invention is not limited to the utilization of these feed media. As will be understood by one of ordinary skill in the art, other feed media may be utilized to grow cells and/or certain alterations may be made to the compositions of the exemplary feed media listed in Table 2. For example, the concentrations of one or more components of such feed media may be increased or decreased to achieve a desired concentration of such components. In certain embodiments, the concentration of each feed medium component is increased or decreased by the same factor. For example, the concentration of each feed medium component may be increased or decreased by 1×, 2×, 3×, 4×, 5×, 6×, 7×, 8×, 9×, 10×, 11×, 12×, 13×, 14×, 15×, 16×, 17×, 18×, 19×, 20×, 25×, 30×, 35×, 40×, 45×, 50× or more.

TABLE 2

Exemplary feed media.

| Amino Acids | Medium F mg/L | Medium F mM | Medium G mg/L | Medium G mM | Medium H mg/L | Medium H mM | Medium I mg/L | Medium I mM | Medium J mg/L | Medium J mM |
|---|---|---|---|---|---|---|---|---|---|---|
| alanine | 17.81 | 0.20 | 213.72 | 2.40 | 214 | 2.40 | 142.47 | 1.60 | 142.48 | 1.60 |
| arginine | 191.07 | 1.10 | 2292 | 13.20 | 2293 | 13.18 | 1528 | 8.79 | 1528 | 8.79 |
| asparagine•H$_2$O | 270.05 | 1.80 | 3240 | 21.60 | 7500 | 50.00 | 1080 | 7.20 | 1080 | 7.20 |
| aspartic acid | 66.66 | 0.50 | 799.92 | 6.00 | 800 | 6.01 | 532.40 | 4.00 | 532.40 | 4.00 |
| cysteine•HCl•H$_2$O | 0.00 | 0.00 | 0.00 | 0.00 | 586 | 1.87 | | | 473.00 | 1.51 |
| cysteine•2HCl | 48.83 | 0.16 | 585.96 | 1.92 | 354 | 2.41 | 470 | 1.50 | 235.38 | 1.60 |
| glutamic acid | 29.47 | 0.20 | 353.64 | 2.40 | 214 | 2.40 | 235.38 | 1.60 | 142.48 | 1.60 |
| monosodium glutamate | | | | | | | | | | |
| glutamine | 456.25 | 3.13 | 5475 | 37.56 | | | 6000 | 41.10 | 4820 | 33.01 |
| glycine | 15.01 | 0.20 | 180.12 | 2.40 | 180 | 2.40 | 120.07 | 1.60 | 120.07 | 1.60 |
| histidine•HCl•H$_2$O | 73.53 | 0.35 | 882.36 | 4.20 | 882 | 4.20 | 588.33 | 2.80 | 588.32 | 2.80 |
| isoleucine | 118.05 | 0.90 | 1416 | 10.80 | 1417 | 10.81 | 944.52 | 7.21 | 944.52 | 7.21 |
| leucine | 170.07 | 1.30 | 2040 | 15.60 | 2041 | 15.58 | 1360 | 10.39 | 1360 | 10.39 |
| lysine•HCl | 182.07 | 1.00 | 2184 | 12.00 | 2185 | 12.00 | 1456 | 8.00 | 1456 | 8.00 |
| methionine | 59.62 | 0.40 | 715.44 | 4.80 | 715 | 4.80 | 477.06 | 3.20 | 477.06 | 3.20 |
| phenylalanine | 82.53 | 0.50 | 990.36 | 6.00 | 990 | 6.00 | 660.36 | 4.00 | 660.36 | 4.00 |
| proline | 69.03 | 0.60 | 828.36 | 7.20 | 828 | 7.20 | 552.31 | 4.80 | 552.31 | 4.80 |
| serine | 158.06 | 1.51 | 1896 | 18.12 | 1897 | 18.06 | 1264 | 12.04 | 1264 | 12.04 |
| threonine | 95.24 | 0.80 | 1142 | 9.60 | 1143 | 9.60 | 762.02 | 6.40 | 762.02 | 6.40 |
| tryptophan | 32.61 | 0.16 | 391.32 | 1.92 | 391 | 1.92 | 260.94 | 1.28 | 260.94 | 1.28 |
| tyrosine•2Na•2H$_2$O | 104.26 | 0.40 | 1251 | 4.80 | 1251 | 4.79 | 832.62 | 3.19 | 832.62 | 3.19 |
| valine | 93.64 | 0.80 | 1123 | 9.60 | 1124 | 9.60 | 749.21 | 6.40 | 749.21 | 6.40 |

| Vitamins | mg/L | μM | mg/L | μM | mg/L | μM | mg/L | μM | mg/L | μM |
|---|---|---|---|---|---|---|---|---|---|---|
| biotin | 17.81 | 73.00 | 4.92 | 20.16 | 4.92 | 20.17 | 3.28 | 13.44 | 3.28 | 0.01 |
| calcium pantothenate | 191.07 | 401.41 | 54.00 | 113.52 | 54 | 113.49 | 36.02 | 75.67 | 36.02 | 0.08 |
| choline chloride | 270.05 | 1943 | 214.92 | 1545 | 215 | 1545 | 143.28 | 1030 | 143.28 | 1.03 |
| folic acid | 66.66 | 151.27 | 63.72 | 144.60 | 64 | 144.57 | 42.43 | 96.21 | 42.43 | 0.10 |
| inositol | | | 302.52 | 1680 | 303 | 1680 | 201.71 | 1120. | 201.71 | 1.12 |

TABLE 2-continued

Exemplary feed media.

| | Medium F | | Medium G | | Medium H | | Medium I | | Medium J | |
|---|---|---|---|---|---|---|---|---|---|---|
| Amino Acids | mg/L | mM | mg/L | mM | mg/L | mM | mg/L | mM | mg/L | mM |
| nicotinamide | 48.83 | 400.41 | 48.00 | 393.60 | 48 | 393.60 | 32.018 | 262.44 | 32.02 | 0.26 |
| pyridoxal•HCl | 29.47 | 145.17 | | | 49 | 238.93 | | | | |
| pyridoxine•HCl | 456.25 | 2215 | 49.20 | 238.92 | 5.4 | 14.37 | 32.82 | 159.32 | 32.82 | 0.16 |
| riboflavin | 15.01 | 39.92 | 5.40 | 14.40 | 303 | 275.43 | 3.60 | 9.57 | 3.60 | 0.01 |
| thiamine•HCl | 73.53 | 218.19 | 92.88 | 275.40 | 93 | 12.40 | 35.22 | 104.51 | 35.22 | 0.10 |
| vitamin B12 | 118.05 | 87.12 | 16.80 | 12.36 | 17 | 20.17 | 11.21 | 8.27 | 11.21 | 0.01 |
| Inorganic Salts | mg/L | mM | mg/L | mM | mg/L | mM | mg/L | mM | mg/L | mM |
| $CaCl_2$ | | | | | | | 113.27 | 1.02 | | |
| KCl | | | | | | | | | | |
| $KH_2PO_4$ | | | | | | | 1640 | 12.06 | 1635 | 12.02 |
| $Na_2HPO_4$ | | | | | 1566 | 11.35 | | | | |
| NaCl | | | | | | | | | | |
| $NaH_2PO_4 \cdot H_2O$ | 130.50 | 0.95 | 1566.00 | 11.40 | | | | | | |
| $MgSO_4$ | | | | | | | | | | |
| $MgSO_4 \cdot 7H_2O$ | 21.50 | 0.09 | 258.00 | 1.08 | 258 | 1.05 | 170 | 0.690 | 171.98 | 0.70 |
| $MgCl_2$ | | | | | | | | | | |
| $NaHCO_3$ | | | | | | | | | | |
| Trace Elements | μg/L | nM | μg/L | nM | μg/L | nM | μg/L | nM | μg/L | nM |
| Sodium Selenite | 5.00 | 28.92 | 60.00 | 347.04 | 60.00 | 347.02 | 40 | 231.35 | 40.00 | 231.35 |
| $CuSO_4$ | 0.43 | 2.69 | 5.16 | 32.28 | 5.16 | 32.26 | 3.44 | 21.51 | 3.44 | 21.51 |
| $CuSO_4 \cdot 5H_2O$ | 1.54 | 6.19 | 18.48 | 74.28 | 18.54 | 74.24 | 7.49 | 30.00 | 7.49 | 30.00 |
| $FeSO_4 \cdot 7H_2O$ | 571.64 | 2056 | 6859 | 24675 | 6859 | 24675 | 2534 | 9115 | 2534 | 9115 |
| $ZnSO_4 \cdot 7H_2O$ | 408.08 | 1421 | 4896 | 17062 | 4897 | 17062 | 2704 | 9421 | 2704 | 9421 |
| $MnSO_4 \cdot H_2O$ | 0.10 | 0.57 | 1.20 | 6.84 | 1.15 | 6.79 | 0.17 | 1.01 | 0.17 | 1.01 |
| $Na_2SiO_3 \cdot 9H_2O$ | 78.75 | 277.22 | 945.00 | 3326 | 945.00 | 3326 | 140 | 492.84 | 140 | 492.84 |
| $(NH_4)_6Mo_7O_{24} \cdot 4H_2O$ | 0.70 | 0.56 | 8.40 | 6.72 | 8.37 | 6.77 | 1.24 | 1.00 | 1.24 | 1.00 |
| $NH_4VO_3$ | 0.37 | 3.13 | 4.44 | 37.56 | 4.39 | 37.50 | 0.65 | 5.56 | 0.65 | 5.56 |
| $NiSO_4 \cdot 6H_2O$ | 0.07 | 0.28 | 0.84 | 3.36 | 0.88 | 3.34 | 0.13 | 0.49 | 0.13 | 0.49 |
| $SnCl_2 \cdot 2H_2O$ | 0.07 | 0.30 | 0.84 | 3.60 | 0.81 | 3.59 | 0.12 | 0.53 | 0.12 | 0.53 |
| $AlCl_3 \cdot 6H_2O$ | | | | | | | 1.2 | 4.97 | 1.20 | 4.97 |
| $AgNO_3$ | | | | | | | 0.17 | 1.00 | 0.17 | 1.00 |
| $Ba(C_2H_3O_2)_2$ | | | | | | | 2.55 | 9.98 | 2.55 | 9.98 |
| KBr | | | | | | | 0.12 | 1.01 | 0.12 | 1.01 |
| $CdCl_2 \cdot 2.5H_2O$ | | | | | | | 2.28 | 9.99 | 2.28 | 9.99 |
| $CoCl_2 \cdot 6H_2O$ | | | | | | | 2.38 | 10.00 | 2.38 | 10.00 |
| $CrCl_3$ | | | | | | | 0.32 | 2.02 | 0.32 | 2.02 |
| NaF | | | | | | | 4.2 | 100.02 | 4.20 | 100.02 |
| $GeO_2$ | | | | | | | 0.53 | 5.07 | 0.53 | 5.07 |
| KI | | | | | | | 0.17 | 1.02 | 0.17 | 1.02 |
| RbCl | | | | | | | 1.21 | 10.01 | 1.21 | 10.01 |
| $ZrOCl_2 \cdot 8H_2O$ | | | | | | | 3.22 | 9.99 | 3.22 | 9.99 |
| Other Components | mg/L | μM | mg/L | μM | mg/L | μM | mg/L | μM | mg/L | μM |
| Hydrocortisone | 0.04 | 0.10 | 0.48 | 1.20 | 0.432 | 1.19 | 0.288 | 0.794 | 0.288 | 0.79 |
| Putrescine•2HCl | 1.00 | 6.21 | 12.00 | 74.52 | 12 | 74.49 | 8 | 49.66 | 8 | 49.66 |
| linoleic acid | 0.04 | 0.15 | 0.48 | 1.80 | 0.505 | 1.80 | 0.336 | 1.20 | 0.336 | 1.20 |
| thioctic acid | 0.11 | 0.51 | 1.32 | 6.12 | 1.26 | 6.13 | 0.841 | 4.08 | 0.841 | 4.08 |
| D-glucose (Dextrose) | 4194.14 | 23300 | 50329 | 279609 | 50330 | 279609 | 43005 | 238922 | 33005 | 183.37 |
| PVA | 200.00 | | 2400 | | | | 2400 | | 2400 | |
| Nucellin | 10.00 | | 120.00 | | | | 80 | | 80.00 | |
| Sodium Pyruvate | | | | | | | | | | |

Example 2

Effects of Addition of Copper and Glutamate to Defined Growth Media

Introduction: One challenge in the expression of proteins or polypeptides in a cell culture is the minimization of misfolded or aggregated versions of the expressed protein or polypeptide. Several solutions to this problem have been proposed, including lowering the pH and/or temperature of the cell culture, as well as addition of induction agents such as HMBA.

To determine whether the redox environment of the cell culture played a role in the accumulation of misfolded and aggregated polypeptides, the following experiments were carried out. To achieve a more oxidized environment, copper and glutamate were added to cell culture media, based on their known intracellular mechanisms that influence redox states. Copper catalyzes the extra-cellular oxidation of cysteine (the reduced form) to cystine (the oxidized form). It was hypothesized that adding copper to a cell culture medium would facilitate the accumulation of cystine, creating a more oxidized environment. Glutamate has been shown to interfere with the ability of cells to take up cystine and reduce it to cysteine. It was thought that by using glutamate to block the cell's ability to uptake cystine and subsequent convert it to cysteine, a more oxidized environment would result.

Material and Methods: For all the following experiments, TNFR-Ig was grown in 1 L production bioreactors, following standard perfusion methods. Each cell culture for a particular set of experiments (as indicated in Tables 3, 4, and 5) was seeded from the same inoculum source. The pH and temperature set points were modified slightly between experiments, the details of which are indicated in Tables 3, 4 and 5. Copper and glutamate were administered to the initial cell culture on Day 0 of the production run. The induction agents HMBA and NaB were added to the cell cultures at times indicated in Tables 3, 4, and 5.

Each cell culture was initially grown at a first temperature and then shifted to a lower temperature on day 1. At the end of each experiment, cell-free conditioned media were stored at −80° C. Protein preparations were carried out on the thawed material following standard protocols. Product quality analyses were conducted using the column eluate retained from each of the tested cell culture conditions.

TABLE 3

Experiment 1: Evaluation of Addition of Copper or Glutamate to Cell Culture Growth Media.

|  | Copper (30° C., pH 6.95) | Glutamate (30° C., pH 6.95) | Control (30° C., pH 6.95) |
| --- | --- | --- | --- |
| Temperature Setpoint | 37° C. | 37° C. | 37° C. |
| pH Setpoint | 6.95 +/− .02 | 6.95 +/− .02 | 6.95 +/− .02 |
| DO Setpoint | 60 | 60 | 60 |
| Copper | 1 μM | — | — |
| Glutamate | — | 5 mM | — |
| Feed Rate | 5% on days 3, 6, and 8 | 5% on days 3, 6, and 8 | 5% on days 3, 6, and 8 |
| Induction Agents | 3 mM HMBA | 3 mM HMBA | 3 mM HMBA |
| Induction Day | D 1 | D 1 | D 1 |
| Induction Agents | 1 mM NaB | 1 mM NaB | 1 mM NaB |
| Induction Day | D 1 | D 1 | D 1 |
| $2^{nd}$ Temperature | 30° C. | 30° C. | 30° C. |
| Temperature Shift Day | D 1 | D 1 | D 1 |

TABLE 4

Experiment 2: Evaluation of Addition of Copper, Glutamate or Both to Cell Culture Growth Media.

|  | Glutamate (30° C., pH 6.95) | Copper (30° C., pH 6.95) | Combo (30° C., pH 6.95) | Control (30° C., pH 6.95) | Copper (29.5° C., pH 6.85) | Control (29.5° C., pH 6.85) |
| --- | --- | --- | --- | --- | --- | --- |
| Temperature Setpoint | 37° C. | 37° C. | 37° C. | 37° C. | 37° C. | 37° C. |
| pH Setpoint | 6.95 +/− .02 | 6.95 +/− .02 | 6.95 +/− .02 | 6.95 +/− .02 | 6.85 +/− .02 | 6.85 +/− .02 |
| DO Setpoint | 60 | 60 | 60 | 60 | 60 | 60 |
| Copper | — | 1 μM | 1 μM | — | 1 μM | — |
| Glutamate | 5 mM | — | 5 mM | — | — | — |
| Feed Rate | 5% on days 3, 6, and 8 | 5% on days 3, 6, and 8 | 5% on days 3, 6, and 8 | 5% on days 3, 6, and 8 | 5% on days 3, 6, and 8 | 5% on days 3, 6, and 8 |
| Induction Agents | 3 mM HMBA | 3 mM HMBA | 3 mM HMBA | 3 mM HMBA | 3 mM HMBA | 3 mM HMBA |
| Induction Day | D1 | D1 | D1 | D1 | D1 | D1 |
| Induction Agents | 1 mM NaB | 1 mM NaB | 1 mM NaB | 1 mM NaB | 1 mM NaB | 1 mM NaB |
| Induction Day | D1 | D1 | D1 | D1 | D1 | D1 |
| $2^{nd}$ Temperature | 30° C. | 30° C. | 30° C. | 30° C. | 29.5° C. | 29.5° C. |
| Temperature Shift Day | D1 | D1 | D1 | D1 | D1 | D1 |

TABLE 5

Experiment 3: Evaluation of Addition of Copper, Glutamate or Both to Cell Culture Growth Media.

|  | Combo, extra Cu (29.5° C., pH 6.95) | Combo, low Glu (29.5° C., pH 6.95) | Combo (29.5° C., pH 6.95) | Combo, extra HMBA (29.5° C., pH 6.95) | Control (29.5° C., pH 6.85) | Control (no temp shift) | Combo (no temp shift) |
| --- | --- | --- | --- | --- | --- | --- | --- |
| Temperature Setpoint | 37° C. | 37° C. | 37° C. | 37° C. | 37° C. | 29.5° C. | 29.5° C. |
| pH Setpoint | 6.95 +/− .02 | 6.95 +/− .02 | 6.95 +/− .02 | 6.95 +/− .02 | 6.85 +/− .02 | 6.85 +/− .02 | 6.85 +/− .02 |
| DO Setpoint | 60 | 60 | 60 | 60 | 60 | 60 | 60 |
| Copper | 1.5 μM | 1 μM | 1 μM | 1 μM |  |  | 1 μM |
| Glutamate | 5 mM | 2.5 mM | 5 mM | 5 mM |  |  | 5 mM |

TABLE 5-continued

Experiment 3: Evaluation of Addition of Copper, Glutamate or Both to Cell Culture Growth Media.

| | Combo, extra Cu (29.5° C., pH 6.95) | Combo, low Glu (29.5° C., pH 6.95) | Combo (29.5° C., pH 6.95) | Combo, extra HMBA (29.5° C., pH 6.95) | Control (29.5° C., pH 6.95) | Control (no temp shift) | Combo (no temp shift) |
|---|---|---|---|---|---|---|---|
| Feed Rate | 5% on days 3, 6, 8 and 10 | 5% on days 3, 6, 8 and 10 | 5% on days 3, 6, 8 and 10 | 5% on days 3, 6, 8 and 10 | 5% on days 3, 6, 8 and 10 | 5% on days 3, 6, 8 and 10 | 5% on days 3, 6, 8 and 10 |
| Induction Agents | 3 mM HMBA | 3 mM HMBA | 3 mM HMBA | 4 mM HMBA | 3 mM HMBA | 3 mM HMBA | 3 mM HMBA |
| Induction Day | D1 | D1 | D1 | D1 | D1 | D1 | D1 |
| Induction Agents | 1 mM NaB | 1 mM NaB | 1 mM NaB | 1 mM NaB | 1 mM NaB | 1 mM NaB | 1 mM NaB |
| Induction Day | D1 | D1 | D1 | D1 | D1 | D3 | D3 |
| 2$^{nd}$ Temperature | 29.5° C. | 29.5° C. | 29.5° C. | 29.5° C. | 29.5° C. | — | — |
| Temperature Shift Day | D1 | D1 | D1 | D1 | D1 | — | — |

Figure 2:
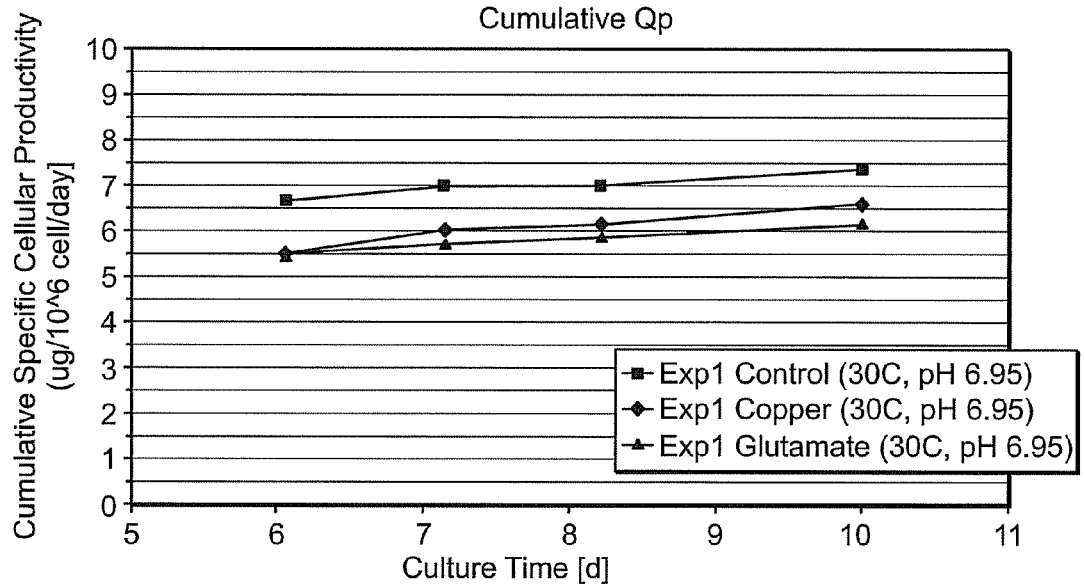
FIG. 2 shows the cumulative specific productivity (Qp) of cell cultures grown under the experimental conditions described in Table 3.
Figure 3:
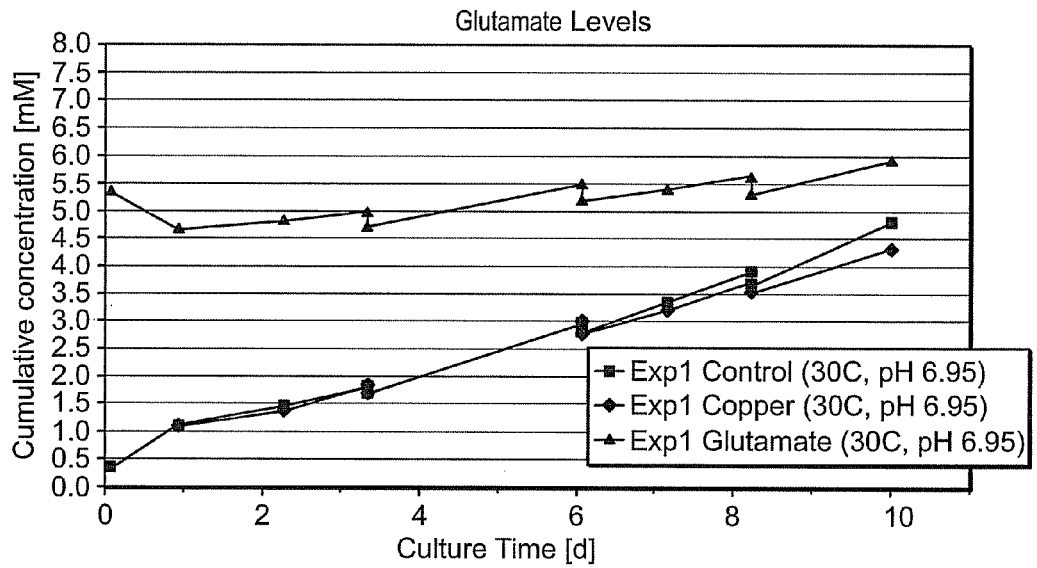
FIG. 3 shows glutamate levels of cell cultures grown under the experimental conditions described in Table 3.
Figure 4:
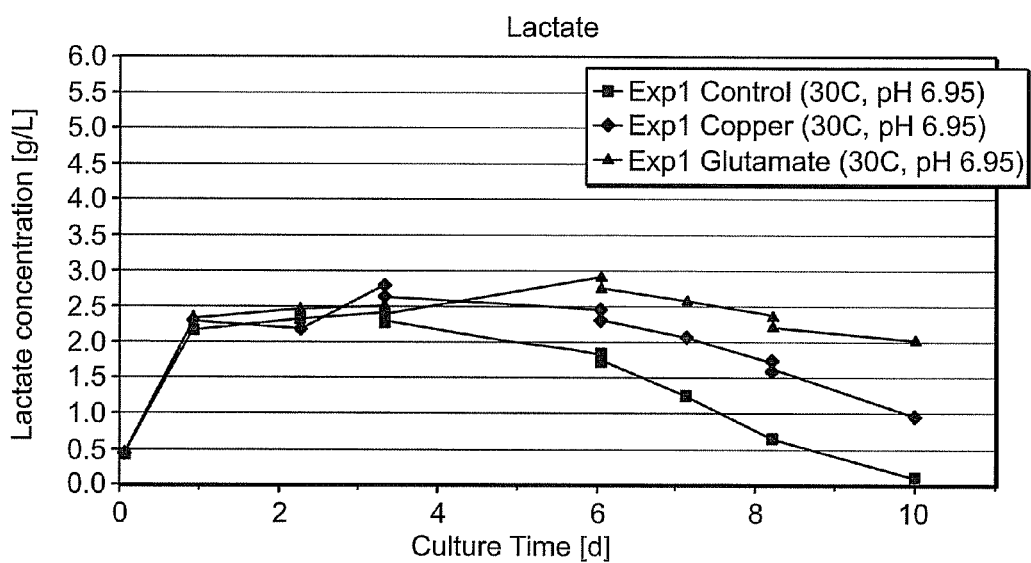
FIG. 4 shows lactate levels of cell cultures grown under the experimental conditions described in Table 3.
Figure 5:
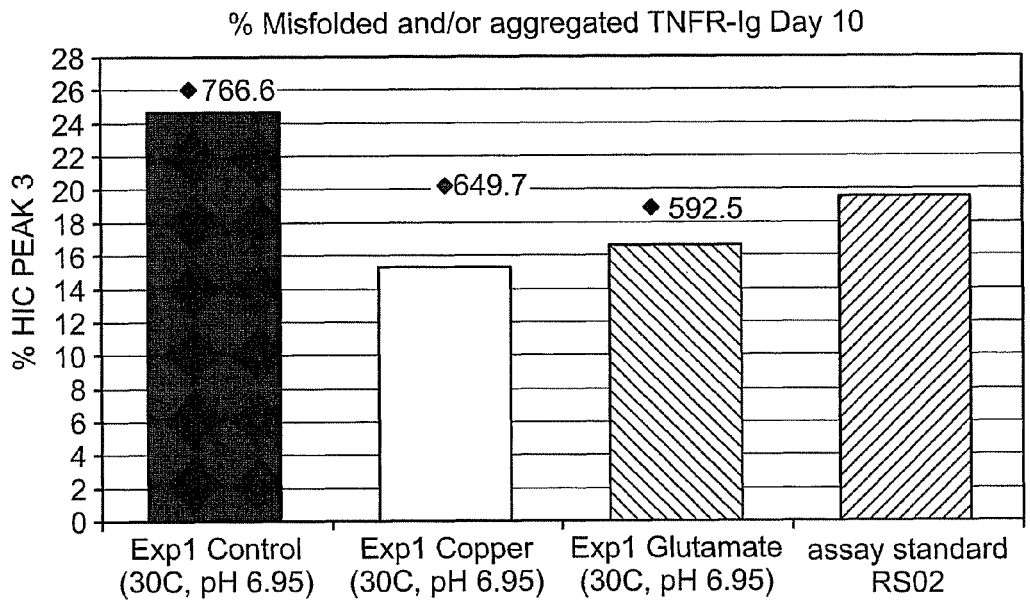
FIG. 5 shows the Day 10 relative level of misfolded and/or aggregated produced TNFR-Ig and the Day 10 titer of cell cultures grown under the experimental conditions described in Table 3.
Figure 6:
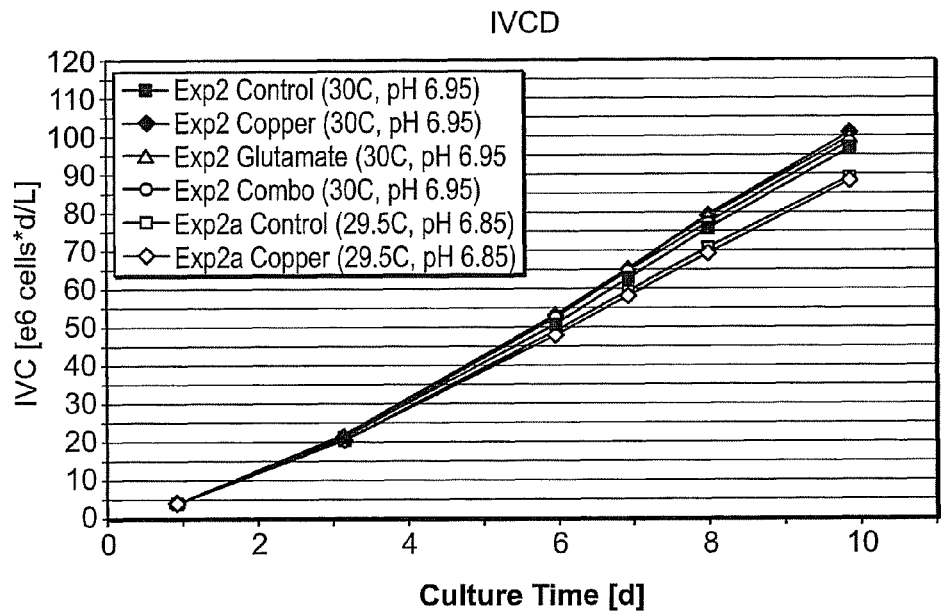
FIG. 6 shows the integrated viable cell density (IVCD) of cell cultures grown under the experimental conditions described in Table 4.
Figure 7:
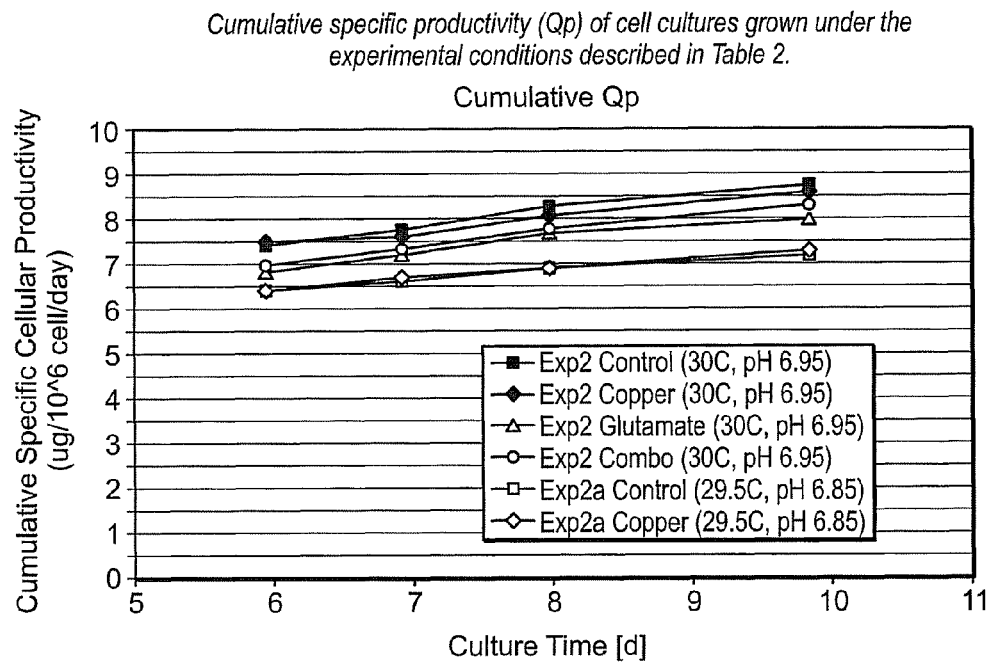
FIG. 7 shows the cumulative specific productivity (Qp) of cell cultures grown under the experimental conditions described in Table 4.
Figure 8:
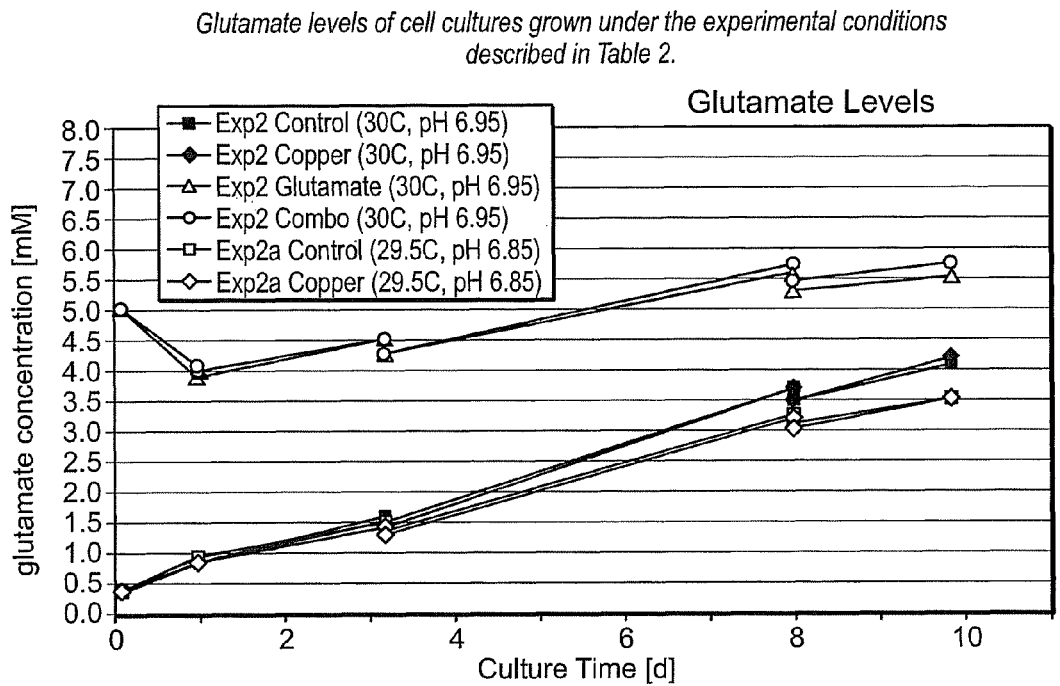
FIG. 8 shows glutamate levels of cell cultures grown under the experimental conditions described in Table 4.
Figure 9:
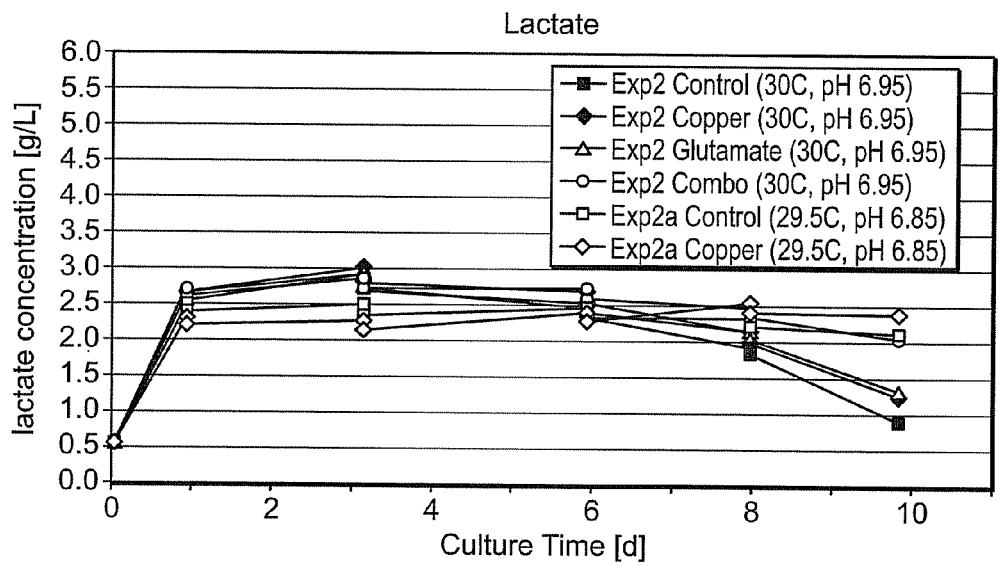
FIG. 9 shows lactate levels of cell cultures grown under the experimental conditions described in Table 4.
Figure 10:
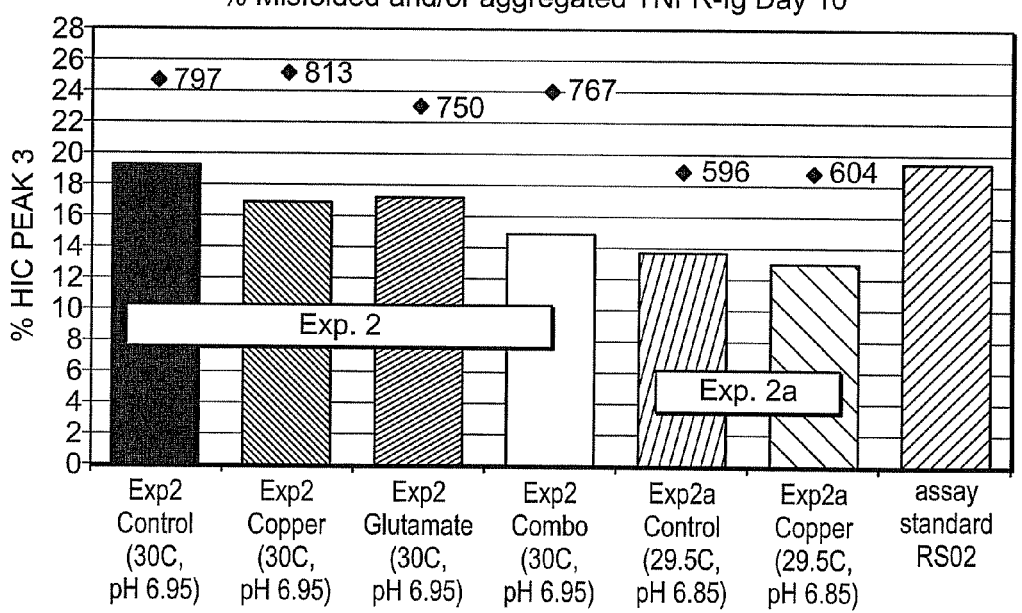
FIG. 10 shows the Day 10 relative level of misfolded and/or aggregated produced TNFR-Ig and the Day 10 titer of cell cultures grown under the experimental conditions described in Table 4.
Figure 11:
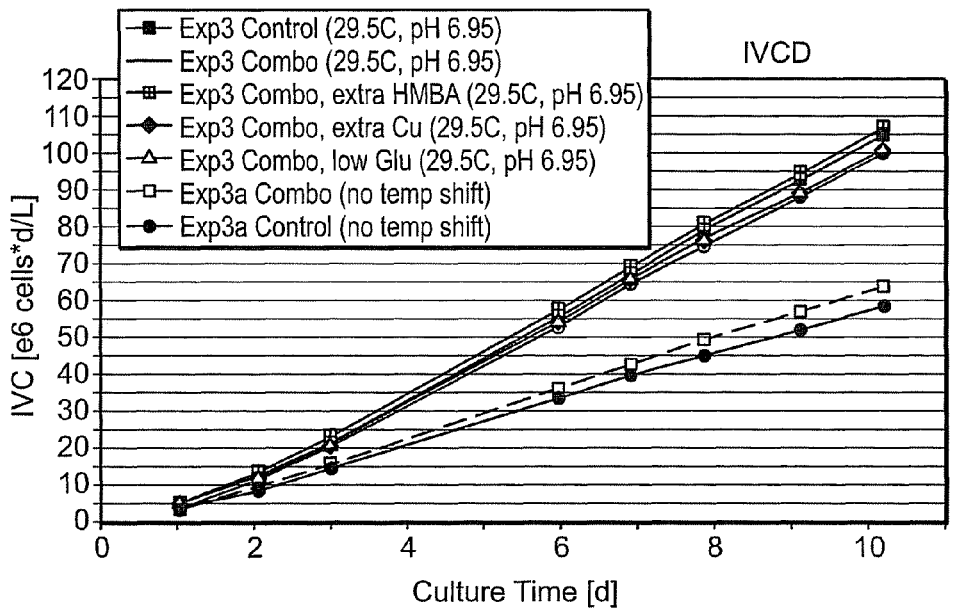
FIG. 11 shows the integrated viable cell density (IVCD) of cell cultures grown under the experimental conditions described in Table 5.
Figure 12:
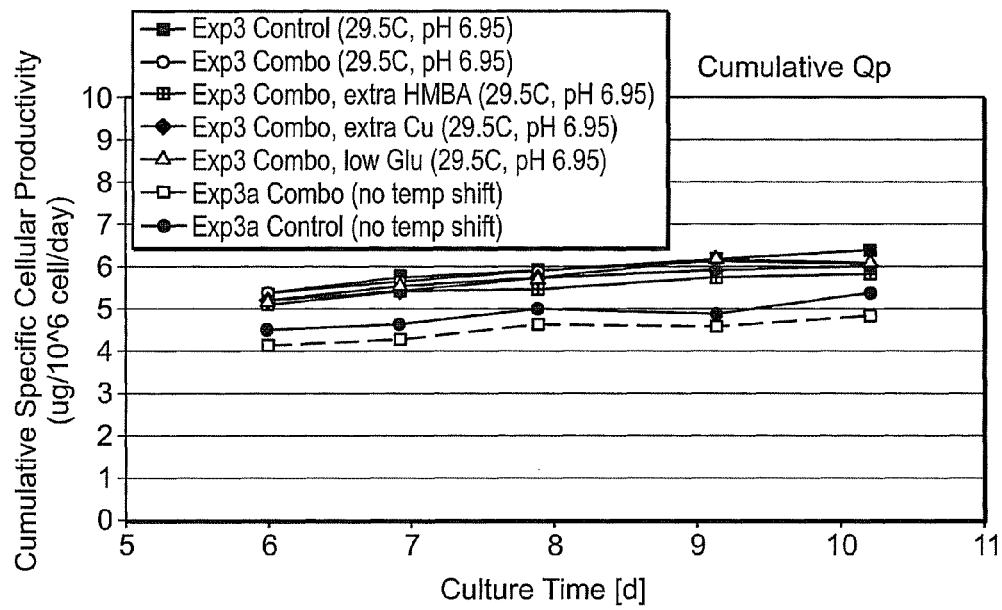
FIG. 12 shows the cumulative specific productivity (Qp) of cell cultures grown under the experimental conditions described in Table 5.
Figure 13:
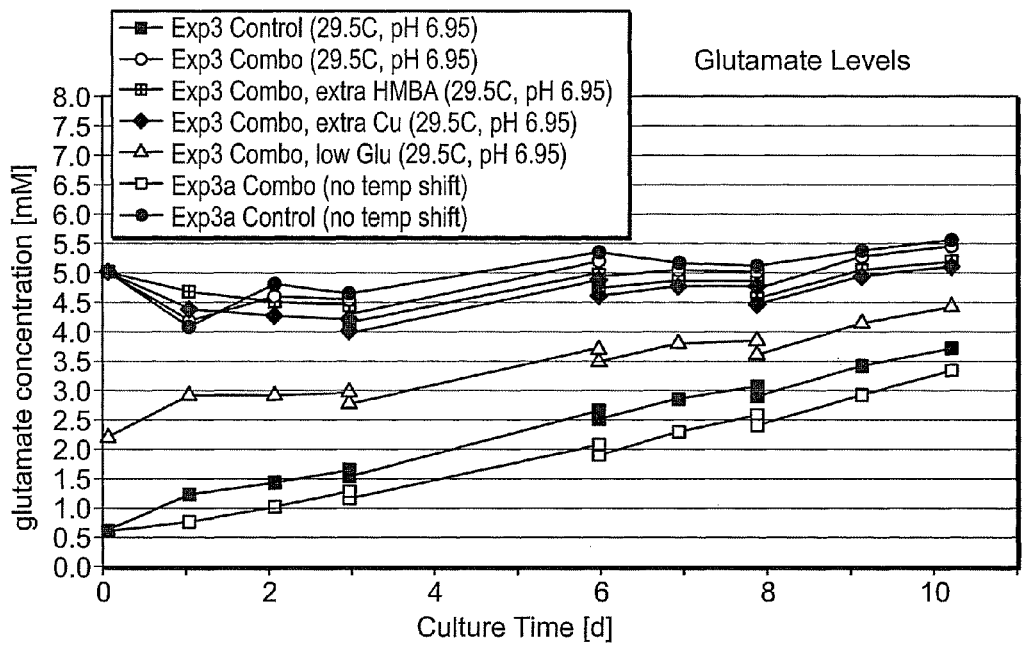
FIG. 13 shows glutamate levels of cell cultures grown under the experimental conditions described in Table 5.
Figure 14:
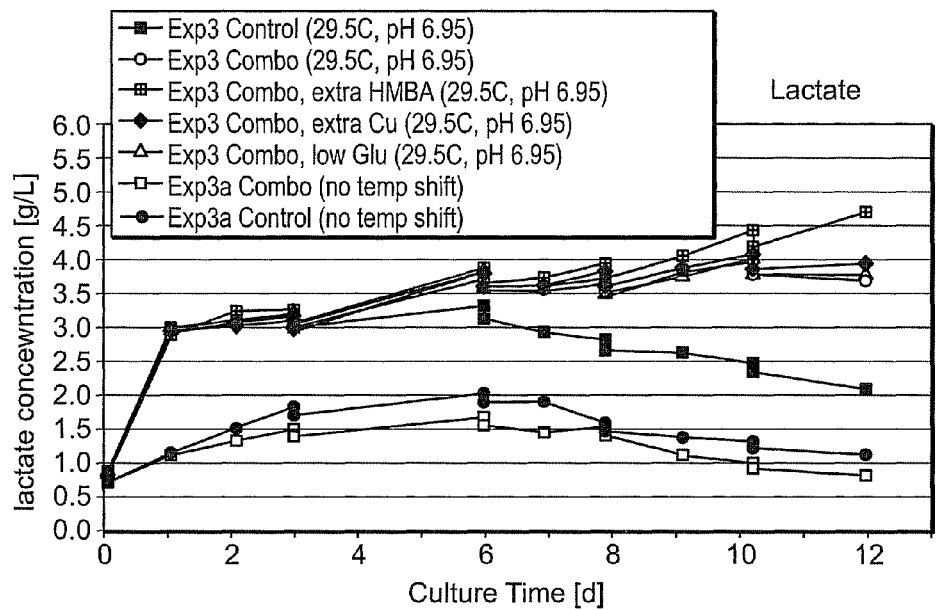
FIG. 14 shows lactate levels of cell cultures grown under the experimental conditions described in Table 5.
Figure 15:
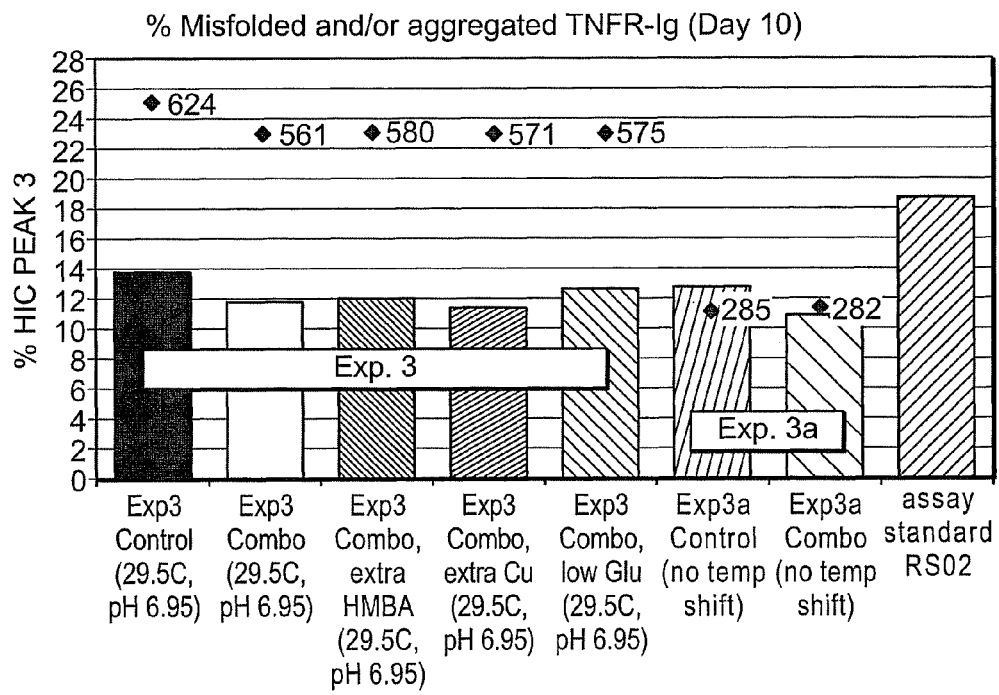
FIG. 15 shows the Day 10 relative level of misfolded and/or aggregated produced TNFR-Ig and the Day 10 titer of cell cultures grown under the experimental conditions described in Table 5.

Results: FIGS. 1-5, 6-10 and 11-15 present the results from the experiments described in Tables 3, 4 and 5, respectively. FIGS. 1, 6 and 11 show the integrated viable cell density (IVCD) for each of the cell cultures tested in each of the three experiments. FIGS. 2, 7 and 12 show the cumulative specific productivity (Qp) for each of the cell cultures tested in each of the three experiments. FIGS. 3, 8, and 13 show the glutamate levels for each of the cell cultures tested in each of the three experiments. FIGS. 4, 9 and 14 show the lactate levels for each of the cell cultures tested in each of the three experiments. FIGS. 5, 10 and 15 show the proportion of misfolded TNFR-Ig on Day 10 of the cell culture as a percentage of the total TNFR-Ig produced, as well as the Day 10 titer for each of the cell cultures tested in each of the three experiments. Table 6 is a compilation of the quality results (percent misfolded/aggregated TNFR-Ig) for each of the cell cultures described in Tables 3, 4 and 5. Additionally, Table 6 shows the total sialylation of the expressed TNFR-Ig as a percent of the total sialylation of a reference sample of TNFR-Ig.

TABLE 6

Summary Table of Polypeptide Quality Results for Experiments Described in Tables 3, 4 and 5.

| Experiment | Condition | Day | % Misfolded/Aggregated | Sialylation (% of reference) |
|---|---|---|---|---|
| 1 | Control (30° C., pH 6.95) | 10 | 25.42 | 91.51 |
| | Copper (30° C., pH 6.95) | 10 | 15.16 | 144.1 |
| | Glutamate (30° C., pH 6.95) | 10 | 16.55 | 101.05 |
| 2 | Control (30° C., pH 6.95) | 8 | 16.58 | 98.50 |
| | | 10 | 19.27 | 92.95 |
| | Copper (30° C., pH 6.95) | 8 | 15.26 | 72.75 |
| | | 10 | 16.84 | 87.54 |
| | Glutamate (30° C., pH 6.95) | 8 | 15.71 | 69.24 |
| | | 10 | 17.12 | 80.78 |
| | Combo (30° C., pH 6.95) | 8 | 14.24 | 71.88 |
| | | 10 | 14.83 | 84.00 |
| | Control (29.5° C., pH 6.85) | 8 | 13.94 | 88.26 |
| | | 10 | 13.79 | 82.41 |
| | Copper (29.5° C., pH 6.85) | 8 | 13.43 | 68.45 |
| | | 10 | 12.93 | 74.26 |
| 3 | Control (29.5° C., pH 6.95) | 8 | 12.29 | 113.02 |
| | | 10 | 13.7 | 107.43 |
| | | 12 | 15.46 | 97.60 |
| | Combo (29.5° C., pH 6.95) | 8 | 11.76 | 115.35 |
| | | 10 | 11.77 | 117.38 |
| | | 12 | 12.13 | 124.55 |
| | Combo, extra HMBA (29.5° C., pH 6.95) | 8 | 11.85 | 117.46 |
| | | 10 | 11.92 | 122.81 |
| | | 12 | 13.13 | 123.57 |
| | Combo, extra Cu (29.5° C., pH 6.95) | 8 | 11.74 | 119.44 |
| | | 10 | 11.35 | 108.53 |
| | | 12 | 11.96 | 115.05 |
| | Combo, low Glu (29.5° C., pH 6.95) | 8 | 12.2 | 117.06 |
| | | 10 | 12.6 | 113.99 |
| | | 12 | 12.54 | 116.77 |
| | Control (no temp shift) | 8 | 10.38 | 126.90 |
| | | 10 | 12.67 | 111.32 |
| | | 12 | 15.64 | 97.91 |
| | Combo (no temp shift) | 8 | 8.97 | 110.22 |
| | | 10 | 10.76 | 110.58 |
| | | 12 | 13.15 | 116.94 |

Figure 16:
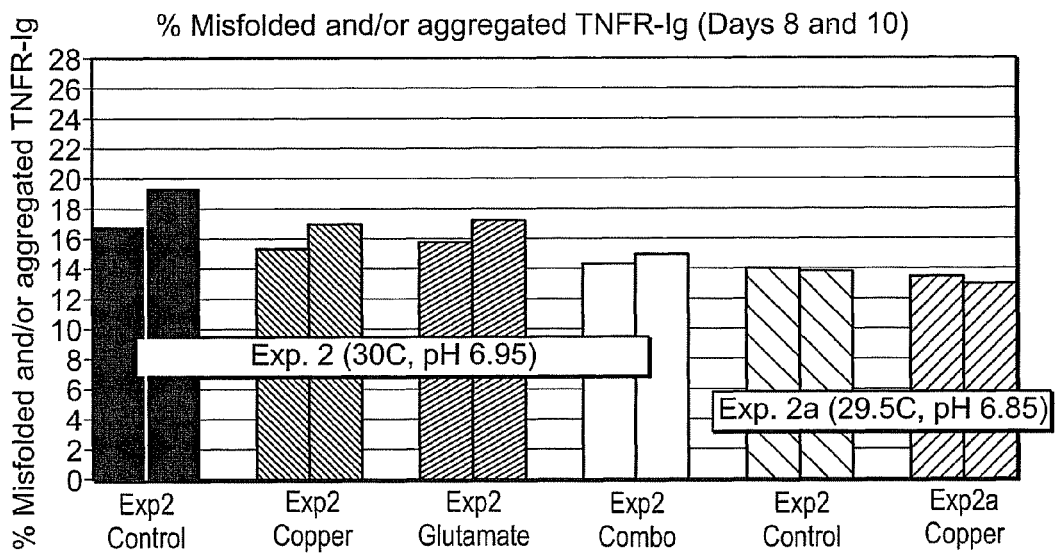
FIG. 16 shows misfolded and/or aggregated TNFR-Ig as a percentage of a reference TNFR-Ig sample on days 8 and 10 for the cell cultures grown under the experimental conditions described in Table 4.
Figure 17:
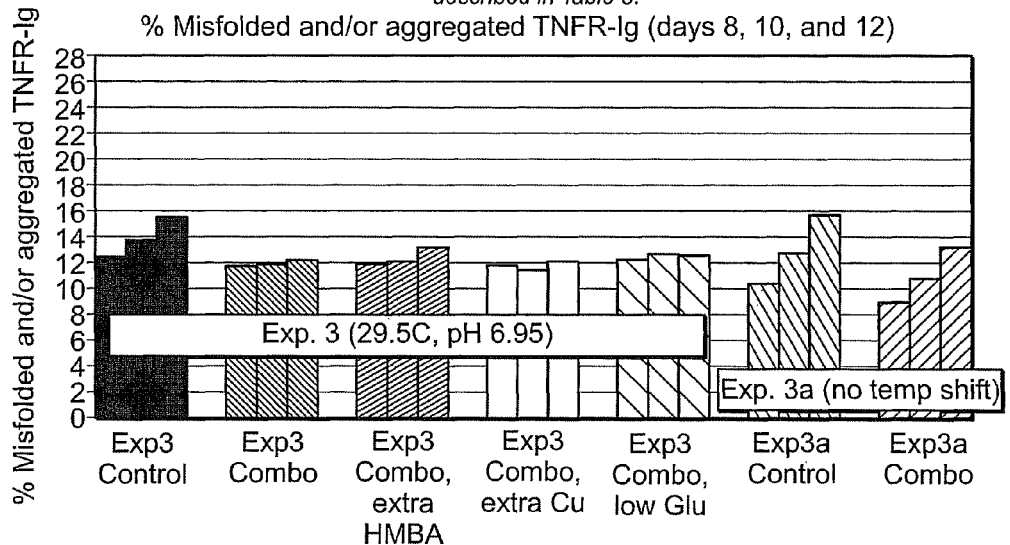
FIG. 17 shows misfolded and/or aggregated TNFR-Ig as a percentage of a reference TNFR-Ig sample on days 8, 10 and 12 for the cell cultures grown under the experimental conditions described in Table 5.
Figure 18:
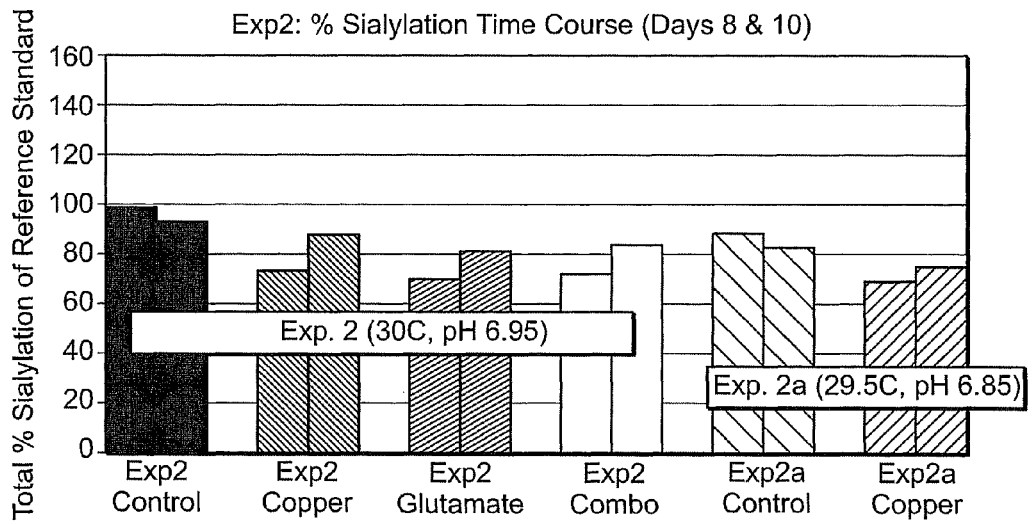
FIG. 18 shows sialylation of expressed TNFR-Ig as a percentage of a reference TNFR-Ig sample on days 8 and 10 for the cell cultures grown under the experimental conditions described in Table 4.
Figure 19:
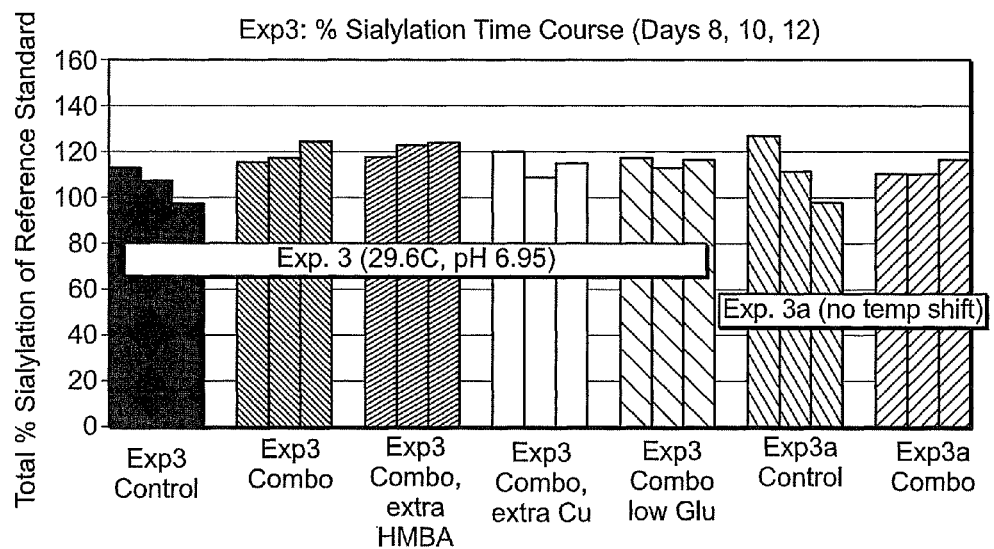
FIG. 19 shows sialylation of expressed TNFR-Ig as a percentage of a reference TNFR-Ig sample on days 8 and 10 for the cell cultures grown under the experimental conditions described in Table 5.

FIGS. 16 and 17 show the percentages of misfolded/aggregated TNFR-Ig on Days 8 and 10 for each of the cell cultures tested for the experiments described in Tables 4 and 5, respectively. FIGS. 18 and 19 show the total sialylation of the expressed TNFR-Ig on Days 8, 10 and 12 as a percent of the total sialylation of a reference sample of TNFR-Ig for the experiments described in Tables 4 and 5, respectively.

Cell Culture Performance: The addition of copper, glutamate or a combination of the two did not significantly impact the culture performance when compared to the control condition within each experiment. The cumulative cell density was not negatively affected by the additions, as shown in FIGS. 1, 6 and 11. As seen in FIGS. 2, 7 and 12, one uniform effect among all the additions was a slight reduction in specific productivity compared to the control, a difference consistently observed in all three experiments. Under most conditions, the harvest titers were slightly lower than the control process, as expected given the small differences in specific productivity rates.

Glutamate accumulation was measured over the course of each production run. As seen in FIGS. 3, 8 and 13, conditions in which glutamate was administered upfront (glutamate-only and combination conditions) had an overall lower glutamate production rate. Although the specific production rate was lower, one uniform effect among these glutamate-containing additions was that the final glutamate concentration was consistently about 1.5 mM higher than the control. Conditions in which only copper was administered were identical to the control condition in terms of the glutamate production profile (see FIGS. 3, 8 and 13). This suggests that the copper-only addition did not impact the normal mechanism of glutamate accumulation.

A decrease in lactate consumption was observed for all conditions in which copper, glutamate or a combination of the two was added (see FIGS. 4, 9 and 14). Thus, these conditions were harvested with higher lactate accumulation compared to the control. Without wishing to be bound by any particular theory, the inventors propose that the inverse trend observed between copper and/or glutamate addition and lactate consumption may be indicative of a relationship between redox states and cellular lactate consumption rates.

Product Quality Effects: The major endpoint of these experiments was to assess the impact on the quality of the produced polypeptide when copper, glutamate or a combination of the two was added to a cell culture. Specifically, these experiments were directed to determining whether addition of copper, glutamate or both might lower the total amount of misfolding and/or aggregating of the produced polypeptide without negatively affecting cell culture performance. As can be seen in Table 6, addition of copper, glutamate or the combination of the two did in fact improve the quality of the produced polypeptide. In all three experiments, the total amount of misfolded and/or aggregated polypeptide was lower in the conditions containing copper and/or glutamate.

Interestingly, the time course data from culture conditions of Experiments 2 and 3 indicated that the total amount of misfolded and/or aggregated polypeptide stabilized over time for those conditions containing copper and/or glutamate (see FIGS. 16 and 17, respectively, and Table 6). The control conditions exhibited a clear increase in misfolded and/or aggregated polypeptide levels over time. This effect was not observed in the modified 'no temperature shift' process (see FIG. 17, Exp3a Control vs. Exp3a Combo), indicating that under certain experimental conditions, a temperature shift is useful in decreasing the amount of misfolded and/or aggregated polypeptide. Overall, it was demonstrated in all three experiments that the total amount of misfolded and/or aggregated polypeptide was lower on a given harvest day (8, 10, or 12) for copper and/or glutamate conditions compared to the control process. Of all the conditions investigated, the combination of glutamate and copper consistently reduced the amount of misfolded and/or aggregated polypeptide at harvest.

One unexpected but promising result was the effect of these various additions on total sialylation. As seen in Table 6, the results of Experiment 1 indicated that both the copper and glutamate conditions had higher total sialylation than the control condition. Furthermore, the time course data from the experiments described in Tables 4 and 5 indicated a stabilization or slight increase in total sialylation over time for those conditions containing copper and/or glutamate (see FIGS. 18 and 19). The control conditions in those experiments exhibited a decrease in total sialylation over time. Additionally, the increase in total sialylation was observed in the low pH culture condition (see Table 6 and FIG. 18) as well as the no temperature shift culture condition (see Table 6 and FIG. 19) suggesting that the mechanism may be independent of process pH and temperature strategy.

The foregoing description is to be understood as being representative only and is not intended to be limiting. Alternative methods and materials for implementing the invention and also additional applications will be apparent to one of skill in the art, and are intended to be included within the scope of the following claims.

What is claimed is:

1. A method of producing a polypeptide in a cell culture comprising steps of: culturing mammalian cells that contain a gene encoding a polypeptide of interest in a cell culture medium comprising between 0.7 and 3 µM copper and between 2.5 and 33 mM glutamate under conditions and for a time sufficient to permit expression of the polypeptide, wherein the fraction of misfolded and/or aggregated polypeptide, relative to the total polypeptide produced, is decreased compared to the fraction of misfolded and/or aggregated polypeptide that would be observed in said medium that lacks copper and glutamate.

2. A method of producing a polypeptide in a cell culture comprising steps of: culturing mammalian cells that contain a gene encoding a polypeptide of interest in a cell culture medium comprising between 0.7 and 3 µM copper and between 2.5 and 33 mM glutamate;

maintaining the culture at a first temperature range for a first period of time sufficient to allow the cells to reproduce to a viable cell density within a range of about 20%-80% of the maximal possible viable cell density if the culture were maintained at the first temperature range;

shifting the culture to a second temperature range, wherein at least one temperature of the second temperature range is lower than the lowest temperature of the first temperature range;

maintaining the culture for a second period of time under conditions and for a time sufficient to permit expression of the polypeptide, wherein the fraction of misfolded and/or aggregated polypeptide, relative to the total polypeptide produced, is decreased compared to the fraction of misfolded and/or aggregated polypeptide that would be observed in said medium that lacks copper and glutamate.

3. The method of claim 2, wherein the first temperature range comprises a temperature range that is approximately 30 to 42 degrees Celsius.

4. The method of claim 2, wherein the second temperature range comprises a temperature range that is approximately 25 to 41 degrees Celsius.

5. The method of claim 2, including a second shifting step subsequent to said first shifting step comprising shifting said culture to a third temperature or temperature range, wherein at least one temperature of the third temperature range is lower than the lowest temperature of the second temperature range.

6. The method of claim 5, wherein the third temperature range comprises a temperature range that is approximately 25 to 40 degrees Celsius.

7. The method of claim 1, wherein the medium comprises an initial glutamine concentration, wherein the initial glutamine concentration of the cell culture medium is less than or equal to 4 mM.

8. The method of claim 1, wherein the cell culture is further supplemented with approximately 2 grams per liter glucose.

9. The method of claim 1, wherein the cell culture is further supplemented with supplementary components.

10. The method of claim 9, wherein the supplementary components are provided in a feed medium.

11. The method of claim 10, wherein the supplementary components are provided at multiple intervals.

12. The method of claim 1, wherein the cell culture medium is defined.

13. The method of claim 12, wherein the defined cell culture medium does not contain added serum or hydrolysates.

14. The method of claim 12, wherein the defined cell culture medium is protein-free.

15. The method of claim 1, wherein the cell culture medium comprises between 0.7 and 1.5 µM copper.

16. The method of claim 15, wherein the cell culture medium comprises 1 µM copper.

17. The method of claim 1, wherein the cell culture medium comprises between 3 and 7 mM glutamate.

18. The method of claim 17, wherein the cell culture medium comprises approximately 5 mM glutamate.

19. A method of producing a polypeptide in a cell culture comprising steps of:
culturing mammalian cells that contain a gene encoding a polypeptide of interest in a cell culture medium comprising between 0.7 and 3 µM copper and between 2.5 and 33 mM glutamate under conditions and for a time sufficient to permit expression of the polypeptide, wherein the glycosylation pattern of the expressed polypeptide is increased relative to the glycosylation pattern that would be observed on the expressed polypeptide in said medium that lacks copper and glutamate.

20. A method of producing a polypeptide in a cell culture comprising steps of:
culturing mammalian cells that contain a gene encoding a polypeptide of interest in a cell culture medium comprising between 0.7 and 3 µM copper and between 2.5 and 33 mM glutamate;
maintaining the culture at a first temperature range for a first period of time sufficient to allow the cells to reproduce to a viable cell density within a range of about 20%-80% of the maximal possible viable cell density if the culture were maintained at the first temperature range;
shifting the culture to a second temperature range, wherein at least one temperature of the second temperature range is lower than the lowest temperature of the first temperature range;
maintaining the culture for a second period of time under conditions and for a time sufficient to permit expression of the polypeptide, wherein the glycosylation pattern of the expressed polypeptide is increased relative to the glycosylation pattern that would be observed on the expressed polypeptide in said medium that lacks copper and glutamate.

21. The method of claim 19, wherein the increased glycosylation pattern of the expressed polypeptide comprises an increase in total sialylation.

22. The method of claim 19, wherein the cell culture medium is defined.

23. The method of claim 22, wherein the defined cell culture medium does not contain added serum or hydrolysates.

24. The method of claim 22, wherein the defined cell culture medium is protein-free.

25. The method of claim 19, wherein the cell culture medium comprises between 0.7 and 1.5 µM copper.

26. The method of claim 25, wherein the cell culture medium comprises 1 µM copper.

27. The method of claim 1, wherein the polypeptide is TNFR-Ig.

28. The method of claim 1, wherein the polypeptide is TNFR-Fc.

29. The method of claim 1, wherein the polypeptide is a polypeptide selected from the group consisting of: an enzyme, a clotting factor, a receptor, an antibody, a hormone, a regulatory factor, an antigen, and a binding agent.

30. The method of claim 29, wherein the polypeptide is an anti-Abeta antibody.

31. The method of claim 1, wherein the step of culturing comprises culturing the mammalian cells in a batch culture.

* * * * *